US008133181B2

(12) United States Patent
Yuk et al.

(10) Patent No.: US 8,133,181 B2
(45) Date of Patent: Mar. 13, 2012

(54) DEVICE, SYSTEM AND METHOD TO MEASURE ABDOMINAL AORTIC ANEURYSM DIAMETER

(75) Inventors: Jongtae Yuk, Redmond, WA (US); Gerald McMorrow, Redmond, WA (US)

(73) Assignee: Verathon Inc., Bothell, WA (US)

( * ) Notice: Subject to any disclaimer, the term of this patent is extended or adjusted under 35 U.S.C. 154(b) by 92 days.

(21) Appl. No.: 12/537,985

(22) Filed: Aug. 7, 2009

(65) Prior Publication Data

US 2010/0036242 A1 Feb. 11, 2010

Related U.S. Application Data

(63) Continuation-in-part of application No. 12/121,721, filed on May 15, 2008.

(60) Provisional application No. 61/094,003, filed on Sep. 3, 2008, provisional application No. 61/087,152, filed on Aug. 7, 2008.

(51) Int. Cl.
*A61B 8/00* (2006.01)

(52) U.S. Cl. ........................ 600/443; 382/128

(58) Field of Classification Search .......... 600/437–465; 382/130–132
See application file for complete search history.

(56) References Cited

U.S. PATENT DOCUMENTS

| | | | | |
|---|---|---|---|---|
| 3,613,069 A | 10/1971 | Cary, Jr. et al. | | 340/3 R |
| 4,431,007 A | 2/1984 | Amazeen et al. | | 128/660 |
| 4,556,066 A | 12/1985 | Semrow | | 128/660 |
| 4,757,821 A | 7/1988 | Snyder | | 128/660 |
| 4,771,205 A | 9/1988 | Mequio | | 310/334 |
| 4,821,210 A | 4/1989 | Rumbaugh | | 364/518 |
| 4,844,080 A | 7/1989 | Frass et al. | | 128/660.01 |
| 4,926,871 A | 5/1990 | Ganguly et al. | | 128/660.07 |
| 5,058,591 A | 10/1991 | Companion et al. | | 128/661.03 |
| 5,060,515 A | 10/1991 | Kanda et al. | | 73/602 |
| 5,078,149 A | 1/1992 | Katsumata et al. | | 128/662.03 |
| 5,125,410 A | 6/1992 | Misono et al. | | 128/662.06 |
| 5,148,809 A | 9/1992 | Biegeleisen-Knight et al. | | 128/660.07 |

(Continued)

FOREIGN PATENT DOCUMENTS

EP 0 271 214 6/1988

(Continued)

OTHER PUBLICATIONS

Baker, A., et al.: "Distortion and High-Frequency Generation Due to Nonlinear Propagation of Short Ultrasonic Pulses from a Plane Circular Piston", Journal of Acoustical Society of America, vol. 92, No. 3, pp. 1699-1705, Sep. 1992.

(Continued)

*Primary Examiner* — Sanjay Cattungal
(74) *Attorney, Agent, or Firm* — Foster Pepper PLLC; PG Scott Born; Richard T. Black

(57) ABSTRACT

Systems, methods, and ultrasound transceivers equipped and configured to execute analysis and extract ultrasound information related to an abdominal aortic aneurysm of a subject are described. The methods utilize algorithms to establish improved targeting of the abdominal aortic aneurysm within a region-of-interest. The targeting algorithms may be optimally applied to provide the user with real-time feedback and orientation guidance for positioning the transceiver. Additional methods utilize diameter conversion algorithms to establish the diameter of the abdominal aortic aneurysm based on conversion of the volume measurement and limited segmentation within a targeted region-of-interest of the aorta.

8 Claims, 16 Drawing Sheets

U.S. PATENT DOCUMENTS

| | | | |
|---|---|---|---|
| 5,151,856 A | 9/1992 | Halmann et al. | 364/413.03 |
| 5,159,931 A | 11/1992 | Pini | 128/660.07 |
| 5,197,019 A | 3/1993 | Delon-Martin et al. | 364/563 |
| 5,235,985 A | 8/1993 | McMorrow et al. | 128/660.07 |
| 5,265,614 A | 11/1993 | Hayakawa et al. | 128/602.03 |
| 5,299,577 A | 4/1994 | Brown et al. | 128/660.07 |
| 5,381,794 A | 1/1995 | Tei et al. | 128/662.03 |
| 5,432,310 A | 7/1995 | Stoeger | 200/82 R |
| 5,435,310 A | 7/1995 | Sheehan et al. | 128/653.1 |
| 5,465,721 A | 11/1995 | Kishimoto et al. | 128/660.07 |
| 5,473,555 A | 12/1995 | Potter | 364/724.1 |
| 5,487,388 A | 1/1996 | Rello et al. | 128/660.09 |
| 5,503,152 A | 4/1996 | Oakley et al. | 128/661.01 |
| 5,503,153 A | 4/1996 | Liu et al. | 128/661.08 |
| 5,526,816 A | 6/1996 | Arditi | 128/662.02 |
| 5,553,618 A | 9/1996 | Suzuki et al. | 128/653.1 |
| 5,575,286 A | 11/1996 | Weng et al. | 128/653.1 |
| 5,575,291 A | 11/1996 | Hayakawa et al. | 128/662.03 |
| 5,577,506 A | 11/1996 | Dias | 128/662.03 |
| 5,588,435 A | 12/1996 | Weng et al. | 128/660.07 |
| 5,601,084 A | 2/1997 | Sheehan et al. | 128/661.04 |
| 5,605,155 A | 2/1997 | Chalana et al. | 128/660.07 |
| 5,615,680 A | 4/1997 | Sano | 128/661.09 |
| 5,644,513 A | 7/1997 | Rudin et al. | 364/572 |
| 5,645,077 A | 7/1997 | Foxlin | 128/774 |
| 5,697,525 A | 12/1997 | O'Reilly et al. | 222/105 |
| 5,698,549 A | 12/1997 | Steers et al. | 514/211 |
| 5,724,101 A | 3/1998 | Haskin | 348/441 |
| 5,735,282 A | 4/1998 | Hossack | 128/662.03 |
| 5,738,097 A | 4/1998 | Beach et al. | 128/661.09 |
| 5,776,063 A | 7/1998 | Dittrich et al. | 600/408 |
| 5,782,767 A | 7/1998 | Pretlow, III | 600/443 |
| 5,806,521 A | 9/1998 | Morimoto et al. | 128/661.01 |
| 5,841,889 A | 11/1998 | Seyed-Bolorforosh | 382/128 |
| 5,846,202 A | 12/1998 | Ramamurthy et al. | 600/450 |
| 5,851,186 A | 12/1998 | Wood et al. | 600/437 |
| 5,873,829 A | 2/1999 | Kamiyama et al. | 600/443 |
| 5,892,843 A | 4/1999 | Zhou et al. | 382/176 |
| 5,898,793 A | 4/1999 | Karron et al. | 382/131 |
| 5,903,664 A | 5/1999 | Hartley et al. | 382/154 |
| 5,908,390 A | 6/1999 | Matsushima | 600/447 |
| 5,913,823 A | 6/1999 | Hedberg et al. | 600/443 |
| 5,928,151 A | 7/1999 | Hossack et al. | 600/443 |
| 5,945,770 A | 8/1999 | Hanafy | 310/322 |
| 5,964,710 A | 10/1999 | Ganguly et al. | 600/449 |
| 5,971,923 A | 10/1999 | Finger | 600/437 |
| 5,972,023 A | 10/1999 | Tanner et al. | 606/219 |
| 5,980,459 A | 11/1999 | Chiao et al. | 600/447 |
| 5,993,390 A | 11/1999 | Savord et al. | 600/437 |
| 6,008,813 A | 12/1999 | Lauer et al. | 345/424 |
| 6,030,344 A | 2/2000 | Guracar et al. | 600/447 |
| 6,042,545 A | 3/2000 | Hossack et al. | 600/443 |
| 6,048,312 A | 4/2000 | Ishrak et al. | 600/443 |
| 6,063,033 A | 5/2000 | Haider et al. | 600/447 |
| 6,064,906 A | 5/2000 | Langberg et al. | 600/518 |
| 6,071,242 A | 6/2000 | Lin | 600/456 |
| 6,102,858 A | 8/2000 | Hatfield et al. | 600/443 |
| 6,106,465 A | 8/2000 | Napolitano et al. | 600/443 |
| 6,110,111 A | 8/2000 | Barnard | 600/438 |
| 6,117,080 A | 9/2000 | Schwartz | 600/443 |
| 6,122,538 A | 9/2000 | Sliwa, Jr. et al. | 600/407 |
| 6,123,669 A | 9/2000 | Kanda | 600/443 |
| 6,126,598 A | 10/2000 | Entrekin et al. | 600/437 |
| 6,142,942 A | 11/2000 | Clark | 600/443 |
| 6,146,330 A | 11/2000 | Tujino et al. | 600/443 |
| 6,148,095 A | 11/2000 | Prause et al. | 382/131 |
| 6,151,404 A | 11/2000 | Pieper | 382/128 |
| 6,159,150 A | 12/2000 | Yale et al. | 600/437 |
| 6,171,248 B1 | 1/2001 | Hossack et al. | 600/459 |
| 6,193,657 B1 | 2/2001 | Drapkin | 600/437 |
| 6,200,266 B1 | 3/2001 | Shokrollahi et al. | 600/438 |
| 6,210,327 B1 | 4/2001 | Brackett et al. | 600/437 |
| 6,213,949 B1 | 4/2001 | Ganguly et al. | 600/449 |
| 6,213,951 B1 | 4/2001 | Krishnan et al. | 600/458 |
| 6,222,948 B1 | 4/2001 | Hossack et al. | 382/294 |
| 6,233,480 B1 | 5/2001 | Hochman et al. | 600/476 |
| 6,238,344 B1 | 5/2001 | Gamelsky et al. | 600/437 |
| 6,248,070 B1 | 6/2001 | Kanda et al. | 600/443 |
| 6,254,539 B1 | 7/2001 | Pang et al. | 600/443 |
| 6,264,609 B1 | 7/2001 | Herrington et al. | 600/443 |
| 6,272,469 B1 | 8/2001 | Koritzinsky et al. | 705/2 |
| 6,277,073 B1 | 8/2001 | Bolorforosh et al. | 600/437 |
| 6,286,513 B1 | 9/2001 | Au et al. | 128/898 |
| 6,302,845 B2 | 10/2001 | Shi et al. | 600/438 |
| 6,309,353 B1 | 10/2001 | Cheng et al. | 600/437 |
| 6,325,758 B1 | 12/2001 | Carol et al. | 600/439 |
| 6,338,716 B1 | 1/2002 | Hossack et al. | 600/459 |
| 6,343,936 B1 | 2/2002 | Kaufman et al. | 434/262 |
| 6,346,124 B1 | 2/2002 | Geiser et al. | 660/450 |
| 6,350,239 B1 | 2/2002 | Ohad et al. | 600/437 |
| 6,359,190 B1 | 3/2002 | Ter-Ovanesyan et al. | 604/361 |
| 6,360,027 B1 | 3/2002 | Hossack et al. | 382/294 |
| 6,375,616 B1 | 4/2002 | Soferman et al. | 600/443 |
| 6,400,848 B1 | 6/2002 | Gallagher | 382/254 |
| 6,402,762 B2 | 6/2002 | Hunter et al. | 606/130 |
| 6,406,431 B1 | 6/2002 | Barnard et al. | 600/443 |
| 6,409,665 B1 | 6/2002 | Scott et al. | 600/437 |
| 6,440,071 B1 | 8/2002 | Slayton et al. | 600/437 |
| 6,440,072 B1 | 8/2002 | Schuman et al. | 600/437 |
| 6,443,894 B1 | 9/2002 | Sumanaweera et al. | 600/443 |
| 6,468,218 B1 | 10/2002 | Chen et al. | 600/443 |
| 6,485,423 B2 | 11/2002 | Angelsen et al. | 600/458 |
| 6,491,631 B2 | 12/2002 | Chiao et al. | 600/443 |
| 6,494,841 B1 | 12/2002 | Thomas et al. | 600/447 |
| 6,503,204 B1 | 1/2003 | Sumanaweera et al. | 600/459 |
| 6,511,325 B1 | 1/2003 | Lalka et al. | 434/272 |
| 6,511,426 B1 | 1/2003 | Hossack et al. | 600/437 |
| 6,511,427 B1 | 1/2003 | Sliwa, Jr. et al. | 600/438 |
| 6,515,657 B1 | 2/2003 | Zanelli | 345/419 |
| 6,524,249 B2 | 2/2003 | Moehring et al. | 600/438 |
| 6,535,759 B1 | 3/2003 | Epstein et al. | 600/547 |
| 6,540,679 B2 | 4/2003 | Slayton et al. | 600/439 |
| 6,544,179 B1 | 4/2003 | Schmiesing et al. | 600/447 |
| 6,545,678 B1 | 4/2003 | Ohazama | 345/427 |
| 6,551,246 B1 | 4/2003 | Ustuner et al. | 600/447 |
| 6,565,512 B1 | 5/2003 | Ganguly et al. | 600/449 |
| 6,569,097 B1 | 5/2003 | McMorrow et al. | 600/437 |
| 6,569,101 B2 | 5/2003 | Quistgaard et al. | 600/459 |
| 6,575,907 B1 | 6/2003 | Soferman et al. | 600/438 |
| 6,585,647 B1 | 7/2003 | Winder | 600/437 |
| 6,610,013 B1 | 8/2003 | Fenster et al. | 600/439 |
| 6,611,141 B1 | 8/2003 | Schulz et al. | 324/226 |
| 6,622,560 B2 | 9/2003 | Song et al. | 73/606 |
| 6,628,743 B1 | 9/2003 | Drummond et al. | 378/8 |
| 6,643,533 B2 | 11/2003 | Knoplioch et al. | 600/407 |
| 6,650,927 B1 | 11/2003 | Keidar | 600/424 |
| 6,676,605 B2 | 1/2004 | Barnard et al. | 600/449 |
| 6,682,473 B1 | 1/2004 | Matsuura et al. | 600/29 |
| 6,688,177 B2 | 2/2004 | Wiesauer | 73/618 |
| 6,695,780 B1 | 2/2004 | Nahum et al. | 600/437 |
| 6,705,993 B2 | 3/2004 | Ebbini et al. | 600/443 |
| 6,716,175 B2 * | 4/2004 | Geiser et al. | 600/450 |
| 6,752,762 B1 | 6/2004 | DeJong et al. | 600/458 |
| 6,755,787 B2 | 6/2004 | Hossack et al. | 600/447 |
| 6,768,811 B2 | 7/2004 | Dinstein et al. | 382/128 |
| 6,780,152 B2 | 8/2004 | Ustuner et al. | 600/443 |
| 6,788,620 B2 | 9/2004 | Shiraishi et al. | 367/152 |
| 6,801,643 B2 * | 10/2004 | Pieper | 382/128 |
| 6,822,374 B1 | 11/2004 | Smith et al. | 310/334 |
| 6,825,838 B2 | 11/2004 | Smith et al. | 345/419 |
| 6,831,394 B2 | 12/2004 | Baumgartner et al. | 310/334 |
| 6,868,594 B2 | 3/2005 | Gururaja | 29/25.35 |
| 6,884,217 B2 | 4/2005 | McMorrow et al. | 600/443 |
| 6,903,813 B2 | 6/2005 | Jung et al. | 356/73 |
| 6,905,467 B2 | 6/2005 | Bradley et al. | 600/443 |
| 6,905,468 B2 * | 6/2005 | McMorrow et al. | 600/443 |
| 6,911,912 B2 | 6/2005 | Roe | 340/573.1 |
| 6,936,009 B2 | 8/2005 | Venkataramani et al. | 600/459 |
| 6,939,301 B2 | 9/2005 | Abdelhak | 600/437 |
| 6,951,540 B2 | 10/2005 | Ebbini et al. | 600/437 |
| 6,954,406 B2 | 10/2005 | Jones | 367/152 |
| 6,961,405 B2 | 11/2005 | Scherch | 378/65 |
| 6,962,566 B2 | 11/2005 | Quistgaard et al. | 600/437 |
| 6,970,091 B2 | 11/2005 | Roe | 340/573.1 |
| 7,004,904 B2 | 2/2006 | Chalana et al. | 600/443 |
| 7,025,725 B2 | 4/2006 | Dione et al. | 600/443 |
| 7,041,059 B2 | 5/2006 | Chalana et al. | 600/437 |

| | | | |
|---|---|---|---|
| 7,042,386 B2 | 5/2006 | Woodford et al. | 342/25 |
| 7,087,022 B2 | 8/2006 | Chalana et al. | 600/449 |
| 7,090,640 B2* | 8/2006 | Barth et al. | 600/443 |
| 7,141,020 B2 | 11/2006 | Poland et al. | 600/447 |
| 7,142,905 B2 | 11/2006 | Slayton et al. | 600/427 |
| 7,177,677 B2 | 2/2007 | Kaula et al. | 600/546 |
| 7,189,205 B2 | 3/2007 | McMorrow et al. | 600/437 |
| 7,215,277 B2 | 5/2007 | Woodford et al. | 342/25 F |
| 7,255,678 B2 | 8/2007 | Mehi et al. | 600/446 |
| 7,301,636 B2 | 11/2007 | Jung et al. | 356/402 |
| 7,382,907 B2 | 6/2008 | Luo et al. | 382/128 |
| 7,450,746 B2 | 11/2008 | Yang et al. | 382/131 |
| 7,520,857 B2 | 4/2009 | Chalana et al. | 600/446 |
| 7,611,466 B2 | 11/2009 | Chalana et al. | 600/443 |
| 2001/0031920 A1* | 10/2001 | Kaufman et al. | 600/431 |
| 2002/0005071 A1 | 1/2002 | Song et al. | 73/606 |
| 2002/0016545 A1 | 2/2002 | Quistgaard et al. | 600/437 |
| 2002/0072671 A1 | 6/2002 | Chenal et al. | 600/450 |
| 2002/0102023 A1 | 8/2002 | Yamauchi | 382/199 |
| 2002/0133075 A1 | 9/2002 | Abdelhak | 600/443 |
| 2002/0147399 A1 | 10/2002 | Mao et al. | 600/458 |
| 2002/0165448 A1 | 11/2002 | Ben-Haim et al. | 600/424 |
| 2003/0055336 A1 | 3/2003 | Buck et al. | 600/453 |
| 2003/0142587 A1 | 7/2003 | Zeitzew | 367/127 |
| 2003/0174872 A1 | 9/2003 | Chalana et al. | 382/128 |
| 2003/0181806 A1 | 9/2003 | Medan et al. | 600/411 |
| 2003/0216646 A1 | 11/2003 | Angelsen et al. | 600/437 |
| 2003/0229281 A1 | 12/2003 | Barnard et al. | 600/438 |
| 2004/0006266 A1 | 1/2004 | Ustuner et al. | 600/47 |
| 2004/0024302 A1 | 2/2004 | Chalana et al. | 600/407 |
| 2004/0034305 A1 | 2/2004 | Song et al. | 600/447 |
| 2004/0054280 A1* | 3/2004 | McMorrow et al. | 600/437 |
| 2004/0076317 A1 | 4/2004 | Roberts | |
| 2004/0106869 A1 | 6/2004 | Tepper | 600/443 |
| 2004/0127796 A1 | 7/2004 | Chalana et al. | 600/449 |
| 2004/0127797 A1 | 7/2004 | Barnard et al. | 600/449 |
| 2004/0267123 A1 | 12/2004 | McMorrow et al. | 600/443 |
| 2005/0135707 A1 | 6/2005 | Turek et al. | 382/294 |
| 2005/0174324 A1 | 8/2005 | Liberty et al. | 345/156 |
| 2005/0193820 A1 | 9/2005 | Sheljaskow et al. | 73/649 |
| 2005/0212757 A1 | 9/2005 | Marvit et al. | 345/156 |
| 2005/0215896 A1 | 9/2005 | McMorrow et al. | 600/437 |
| 2005/0228276 A1 | 10/2005 | He et al. | 600/437 |
| 2005/0240126 A1 | 10/2005 | Foley et al. | 601/2 |
| 2005/0253806 A1 | 11/2005 | Liberty et al. | 345/156 |
| 2006/0025689 A1 | 2/2006 | Chalana et al. | 600/456 |
| 2006/0056672 A1* | 3/2006 | Barth et al. | 382/131 |
| 2006/0064010 A1 | 3/2006 | Cannon, Jr. et al. | 600/434 |
| 2006/0078501 A1 | 4/2006 | Goertz et al. | 424/9.52 |
| 2006/0079775 A1* | 4/2006 | McMorrow et al. | 600/443 |
| 2006/0111633 A1 | 5/2006 | McMorrow et al. | 600/437 |
| 2006/0235301 A1 | 10/2006 | Chalana et al. | 600/443 |
| 2007/0004983 A1 | 1/2007 | Chalana et al. | 600/443 |
| 2007/0232908 A1 | 10/2007 | Wang et al. | 600/437 |
| 2007/0276247 A1 | 11/2007 | Chalana et al. | 600/447 |
| 2007/0276254 A1* | 11/2007 | Yang et al. | 600/463 |
| 2008/0139938 A1* | 6/2008 | Yang et al. | 600/445 |
| 2008/0146932 A1 | 6/2008 | Chalana et al. | 600/447 |
| 2008/0242985 A1 | 10/2008 | Chalana et al. | 600/443 |
| 2008/0249414 A1 | 10/2008 | Yang et al. | 600/445 |
| 2008/0262356 A1 | 10/2008 | Chalana et al. | 600/447 |
| 2009/0062644 A1 | 3/2009 | McMorrow et al. | 600/437 |
| 2009/0088660 A1 | 4/2009 | McMorrow | 600/546 |
| 2009/0105585 A1 | 4/2009 | Wang et al. | 600/437 |
| 2009/0112089 A1 | 4/2009 | Barnard et al. | 600/443 |
| 2009/0264757 A1 | 10/2009 | Yang et al. | 600/443 |

FOREIGN PATENT DOCUMENTS

| | | |
|---|---|---|
| EP | 1 030 187 | 8/2000 |
| EP | 1 076 318 | 2/2001 |
| GB | 2 391 625 | 2/2004 |
| JP | 7-171149 | 7/1995 |
| JP | 2000-126178 | 5/2000 |
| JP | 2000-126181 | 5/2000 |
| JP | 2000-126182 | 5/2000 |
| JP | 2000-210286 | 8/2000 |
| WO | 01/35339 | 5/2001 |
| WO | 2009/032778 | 3/2009 |

OTHER PUBLICATIONS

Baker, A., et al., "Prediction of Non-Linear Propagation in Water Due to Diagnostic Medical Ultrasound Equipment", Phys. Med Biol., vol. 36, No. 11, pp. 1457-1464, 1991.

Barentsz et al., "Primary Staging of Urinary Bladder Carcinoma: the Role of MRI and a Comparison with CT," European Radiology vol. 6, pp. 129-133, 1996.

Besl, P., et al., "A Method for Registration of 3-D Shapes," IEEE Transaction on Pattern Analysis and Machine Intelligence, vol. 14, No. 2, pp. 239-256, Feb. 1992.

Birnholz, J., et al., "Amniotic Fluid Accumulation in the First Trimester," American Institute of Ultrasound in Medicine, Journal Ultrasound Medicine, vol. 14, pp. 597-602, 1995.

Bishop, S., et al., "Human Tissue-Temperature Rise During Ultrasound Treatments with the Aquaflex Gel Pad." Journal of Athletic Training, vol. 39, No. 2, pp. 126-131, 2004.

Bouakaz, A., et al., "Noninvasive Bladder Volume Measurements Based on Nonlinear Wave Distortion," Ultrasound in Medicine & Biology, vol. 30, No. 4, pp. 469-476, 2004.

Boyle, P., et al, "Prostate Volume Predicts Outcome of Treatment of Benign Prostatic Hyperplasia with Finasteride: Meta-Analysis of Randomized Clinical Trials," Urology, vol. 48, No. 3, pp. 398-405, 1996.

Cascione, C., et al., "Transabdominal Ultrasound Versus Excretory Urography in Preoperative Evaluation of Patients with Prostatism," The Journal of Urology, vol. 137, pp. 883-885, May 1987.

Chamberlain, P., "Amniotic Fluid Volume: Ultrasound Assessment and Clinical Significance," Seminars in Perinateology, vol. 9, No. 4, pp. 163-167, 1985.

Chamberlain, P. "Ultrasound Evaluation of Amniotic Fluid Volume," American Journal of Obstetrics and Gynaecology, vol. 150, No. 3, pp. 250-254, Oct. 1, 1984.

Cheng, X. et al., "Boundary Extraction Method for Three Dimensional Ultrasonic Echo Imaging Using Fuzzy Reasoning and Relaxation Techniques," IEEE, pp. 1610-1614, 1994.

Christensen, M., et al., "Clinical Manifestations of Benign Prostatic Hyperplasia and Indications for Therapeutic Intervention," Benign Prostatic Hyperplasia, Urologic Clinics of North America, vol. 17, No. 3, pp. 509-516, Aug. 1990.

Crowley, P., et al., "The Value of Ultrasound Measurement of Amniotic Fluid Volume in the Management of Prolonged Pregnancies," British Journal of Obstetrics and Gynaecology, vol. 91, pp. 444-448, May 1984.

Cvitkovic-Kuzmic, A., et al., "Sonographic Measurement of Detrusor Muscle Thickness in Healthy Children," Pedatric Nephrology, vol. 16, pp. 1122-1125, 2001.

Cvitkovic-Kuzmic, A., et al., "Ultrasound Assessment of Detrusor Muscle Thickness in Children with Non-Neuropathic Bladder/Sphincter Dysfunction," European Urology, Vo. 41, pp. 214-219, 2002.

Elliott, P., "Interactive Image Segmentation for Radiation Treatment Planning," IBM Systems Journal, vol. 31, No. 4, pp. 620-634, 1992.

Forbes, F., et al., "Bayesian Morphology: Fast Unsupervised Bayesian Image Analysis," Journal of the American Statistical Association, vol. 94, No. 446, pp. 555-568, Jun. 1999.

Gerald, C., et al., "Applied Numerical Analysis," Fifth Edition, Addison-Wesley Publishing Company, Chapter 3, 'Interplation and Curve Fitting,', pp. 210-287.

Gobbi, D., et al. "Real-Time 3D Ultrasound for Intraoperative Surgical Guidance," 8 pgs.

Gramellini, D., et al., "Sonographic Assessment of Amniotic Fluid Volume Between 11 and 24 Weeks of Gestation: Construction of Reference Intervals Related to Gestational Age," Ultrasound Obstetrics Gynaecology, vol. 17, pp. 410-415, 2001.

Grover, J., et al., "Three-Dimensional Method for Determination of Amniotic Fluid Volume in Intrauterine Pockets," vol. 90, No. 6, pp. 1007-1010, Dec. 1997.

Hakenberg, O., et al., "Bladder Wall Thickness in Normal Adults and Men with Mild Lower Urinary Tract Symptoms and Benign Prostatic Enlargement," Neurourology and Urodynamics, vol. 19, pp. 585-593, 2000.

Hakenberg, O., et al., "The Estimation of Bladder Volume by Sonocystrography," Journal of Urology, vol. 130, No. 2, pp. 249-251, Aug. 1983.

Hamilton, M., et al., "Nonlinear Acoustics," Copyright 1998 by Academic Press, Chapter 4, 'Progressive Waves in Lossless and Lossy Fluids,' pp. 65-150.

Holmes, J., et al., "Ultrasonic Studies of the Bladder," The Journal of Urology, vol. 91, pp. 654-663, 1967.

Jeng, C., et al., "Amniotic Fluid Index Measurement with the Four-Quadrant Technique During Pregnancy," The Journal of Reproductive Medicine, Inc., vol. 35, No. 7, pp. 674-677, Jul. 1990.

Jequier, S., et al., "Sonographic Measurements of the Normal Bladder Wall in Children," AJR, vol. 149, pp. 563-566, Sep. 1987.

Jong, et al., "Ultrasound Contrast Agents" ISBN 1-85317-858-4 chapter 3 "Contrast-Specific Imaging Methods".

Khullar, V., et al. "A Novel Technique for Measuring Bladder Wall Thickness in Women Using Transvaginal Ultrasound,"Ultrasound Obestetrics and Gyneacology, vol. 4, pp. 220-223, 1994.

Khullar, V., et al., "Ultrasound: a Noninvasive Screening Test for Detrusor Instability," British Journal of Obstertrics and Gynaecology, vol. 103, pp. 904-908, Sep. 1996.

Kojima, M., et al., "Reversible Change of Bladder Hypertrophy Due to Benign Prostatic Hyperplasia After Surgical Relief of Obstruction," The Journal of Urology, vol. 158, pp. 8993, Jul. 1997.

Kojima, M., et al., "Ultrasonic Estimation of Bladder Weight as a Measure of Bladder Hypertrophy in Men with Infravesical Obstruction: a Preliminary Report," Urology, vol. 47, No. 6, pp. 942-947, 1996.

Krenning, B., et al., "Assessment of Left Ventricular Function by Three-Dimensional Echocardiography," Cardiovascular Ultrasound, 7 pgs., 2003.

Kruczkowski et al., "A Non-Invasive Ultrasonic System to Determine Residual Bladder Volumes", IEEE Engineering in Medicine Biology Society 10th Ann Conf, pp. 1623-1624.

Lea, J., et al., "Registration and Immobilization in Robot-Assisted Surgery," Computer Aided Surgery, vol. 1, No. 2, pp. 80-87, 1995.

Lorensen, W., et al., "Marching Cubes: A High Resolution 3D Surface Construction Algorithm," ACM Siggraph Computer Graphics, vol. 21, No. 4, pp. 163-169, Jul. 1987.

Madsen, F., et al., "Clinical Manifestations of Benign Prostatic Hyperplasia," Advances in Benign Prostatic Hyperplasia, Urologic Clinics of North America, vol. 22, No. 2, pp. 291-298, May 1995.

Magann, E., et al., "Amniotic Fluid Volume Determination," American Journal of Obstetrics and Gyneacology, Vo. 169, No. 2, Part 1, pp. 435-437, 1999.

Magann, E., et al., "Measurement of Amniotic Fluid Volume: Accuracy of Ultrasonography Techniques," American Journal of Obstetrics and Gyneacology, vol. 167, No. 6, pp. 1533-1537, 1992.

Magann, E., et al., "Ultrasound Estimate of Amniotic Fluid Volume: Color Doppler Overdiagnosis of Oligohydramnios," Obstetrics & Gynecology, vol. 98, No. 1, pp. 71-74, Jul. 2001.

Magann, E., et al., "Ultrasound Estamation of Amniotic Fluid Volume Using the Largest Vertical Pocket Containing Umbilical Cord: Measure to or Through the Cord," Ultrasound Obstetrics and Gynecology, vol. 20, pp. 464-467, 2002.

Manieri, C., et al., "The Diagnosis of Bladder Outlet Obstruction in Men by Ultrasound Measurement of Bladder Wall Thickness," The Journal of Urology, vol. 159, 761-765, pp. 761-765, Mar. 1998.

Mann, S., et al., "Novel Technique for Assessing Amniotic Fluid Volume: use of a Three-Dimensional Bladder Scanner," The Journal of Maternal-Fetal Medicine, vol. 9, pp. 308-310, 2000.

Manning, F., et al., "Qualitative Amniotic Fluid Volume Determination by Ultrasound: Antepartum Detection of Intrauterine Growth Retardation," American Journal of Obstetrics and Gynecology, vol. 139, No. 3, pp. 254-258, Feb. 1, 1981.

Martan, A., et al., "Ultrasound Imaging of the Lower Urinary System in Women after Burch Colposuspension," Ultrasound Obstetrics and Gynecology, vol. 17, pp. 58-64, 2001.

Matthews, P. et al., "The Use of Ultrasound in the Investigation of Prostatism," British Journal of Urology, vol. 54, pp. 536-538, 1982.

Merks, E. et al., "Design of a Multilayer Transducer for Acoustic Bladder Volume Assessment," IEEE Transacations on Ultrasonics, Ferroelectrics and Frequency Control, vol. 53, No. 10, pp. 1730-1738, Oct. 2006.

Merks, E., et al., "A KLM-Circuit Model of a Multi-Layer Transducer for Acoustic Bladder Volume Measurements," Ultrasonics, vol. 44, pp. 705-710, Dec. 22, 2006.

Miyashita, H., et al., "Ultrasonic Measurement of Bladder Weight as a Possible Predictor of Acute Urinary Retention in Men with Lower Urinary Tract Symptoms Suggestive of Benign Prostatic Hyperplasia," Ultrasound in Medicine & Biology, vol. 28, No. 8, pp. 985-990, 2002.

Moore, T., "Superiority of the Four-Quadrant Sum Over the Single-Deepest-Pocket Technique in Ultrasonographic Identification of Abnormal Amniotic Fluid Volumes," American Journal of Obstetrics and Gynecology, vol. 163, No. 5, pp. 762-767, 1990.

Muller, L., et al., "Detrusor Thickness in Healthy Children Assessed by a Standardized Ultrasound Method," The Journal of Urology, vol. 166, pp. 2364-2367, Dec. 2001.

Muller, L., et al., "Standardized Ultrasound Method for Assessing Detrusor Muscle Thickness in Children," The Journal of Urology, vol. 164, pp. 134-138, Jul. 2000.

Myles, T., et al., "Four-Quadrant Assessment of Amniotic Fluid Volume: Distribution's Role in Predicting Fetal Outcome," Journal of Obstetrics and Gynecology, vol. 80, No. 5, pp. 769-774, Nov. 1992.

Naya, Y., et al., "Intraobserver and Interobserver Variance in the Measurement of Ultrasound-Estimated Bladder Weight," Ultrasound in Medicine and Biology, vol. 24, No. 5, pp. 771-773, 1998.

Oelke, M., et al., "Increase in Detrusor Wall Thickness Indicates Bladder Outlet Obstruction (BOO) in Men," World Journal of Urology, vol. 19, pp. 443-452, 2002.

Ohashit, G., et al., "Boundary Estimation for Ultrasonic 3-D Imaging," SPIE vol. 1898 Image Processing, pp. 480-486, 1993.

Oomen, JA, et al., "Towards Assessment of Regional Wall Stress of the Left Ventricle Using 3D Ultrasound Imaging," IEEE Computers in Cardiology, vol. 26, pp. 129-132, 1999.

Phelan, J., et al., Amniotic Fluid Volume Assessment with the Four-Quadrant Technique at 36-42 Weeks' Gestation, The Journal of Reproductive Medicine, vol. 32, No. 7, pp. 540-542, Jul. 1987.

Rutherford, S., et al., "The Four-Quadrant Assessment of Amniotic Fluid Volume: An Adjunct to Antepartum Fetal Heart Rate Testing," Journal of Obstetrics and Gynecology, vol. 70, No. 3, Part 1, pp. 353-356, Sep. 1987.

Sagiv, C., et al., "Application of a Semiautomatic Boundary Detection Algorithm for the Assessment of Amniotic Fluid Quantity Form Ultrasound Images," Ultrasound in Medicine and Biology, vol. 25, No. 4, pp. 515-526, 1999.

Sahin, B., et al., "Estimation of the Amniotic Fluid Volume Using the Cavalieri Method on Ultrasound Images," International Journal of Gynecology and Obstetrics, vol. 82, pp. 25-30, 2003.

Santilli, J., et al., "Diagnosis and Treatment of Abdominal Aortic Aneurysms," American Family Physician, vol. 56, No. 4, pp. 1081-1090, Sep. 1997.

Scheinerman, E., "Invitation to Dynamical Systems," Chapter 5, 'Fractals,' Prentice Hall pp. 231-315, 1996.

Schiff, E., et al., "Standardized Measurement of Amniotic Fluid Volume by Correlation of Sonography with Dye Dilution Technique," Obstetrics and Gynecology, vol. 76, No. 1, pp. 44-46, Jul. 1990.

Schrimmer, D., et al., "Sonographic Evaluation of Amniotic Fluid Volume," Clinical Obstetrics and Gynecology, vol. 45, No. 4, pp. 1026-1029, 2002.

Sepulveda W., et al., "Direct Volume Measurement at Midtrimester Amnioinfusion in Relation to Ultrasonographic Indexes of Amniotic Fluid Volume," American Journal of Obstetrics and Gynecology, vol. 170, No. 4, pp. 1160-1163, Apr. 1994.

Shiota, T., et al., "Real-time Three-Dimensional Echocardiography for Determining Right Ventricular Stroke Volume in an Animal Model of Chronic Right Ventricular Volume Overload," Circulation Journal of the American Heart Association, vol. 97, pp. 1897-1900, 1998.

Stangenberg, M., et al., "Amniotic Fluid Volume in Pregnant Diabetics During the Last Trimester," Acta Obstetrics Gynecology Scand, vol. 61, pp. 313-316, 1982.

Szabo, T., et al., "Effects of Nonlinearity on the Estimation of In Situ Values of Acoustic Output Parameters," Journal of Ultrasound in Medicine, American Institute of of Ultrasound in Medicine, vol. 18, No. 1, pp. 33-41, 1999.

Weissman, A., et al., "Sonographic Measurement of Amniotic Fluid Volume in the First Trimester of Pregnancy," American Institute of Ultrasound in Medicine, vol. 15, pp. 771-774, 1996.

* cited by examiner

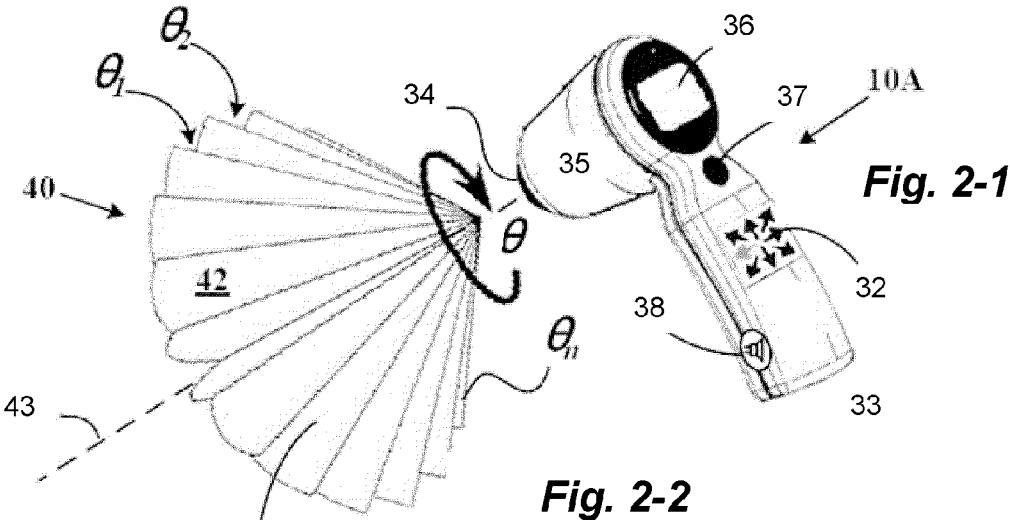
Fig. 2-1
Fig. 2-2
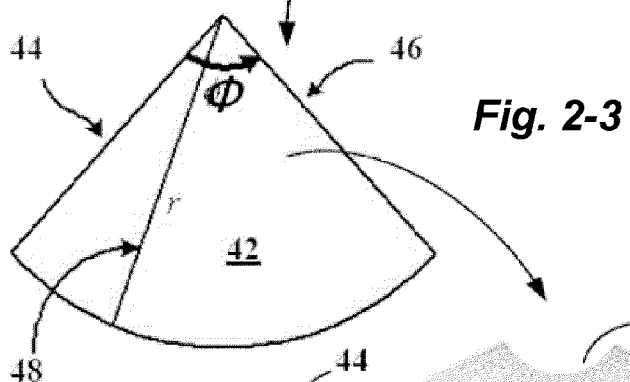
Fig. 2-3
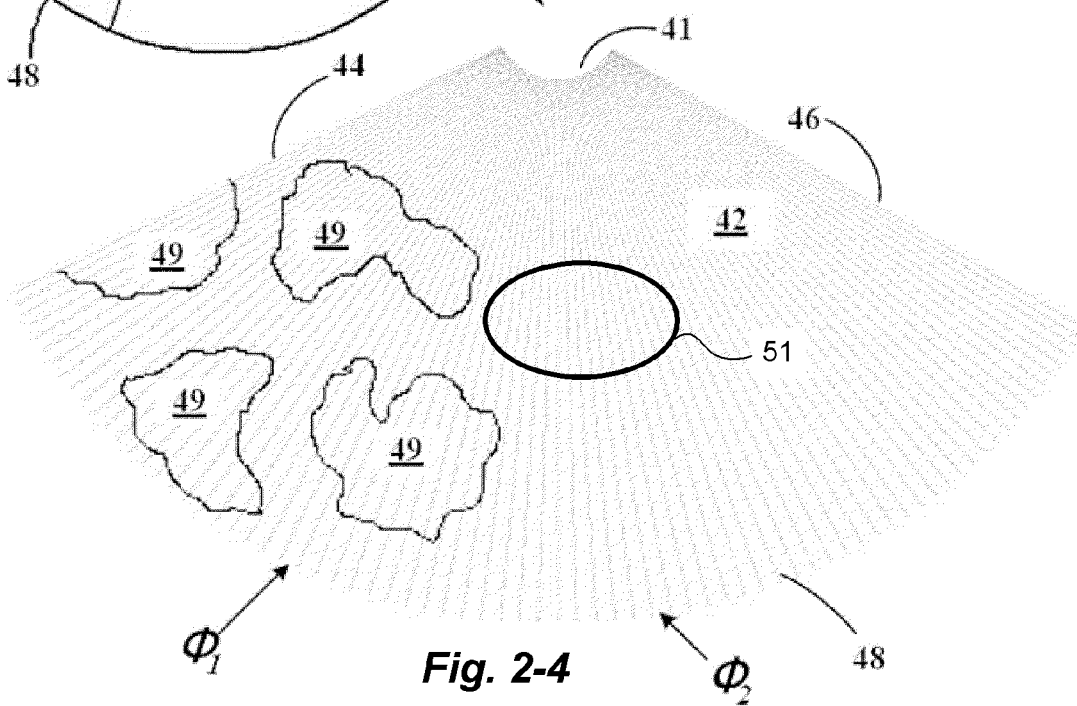
Fig. 2-4

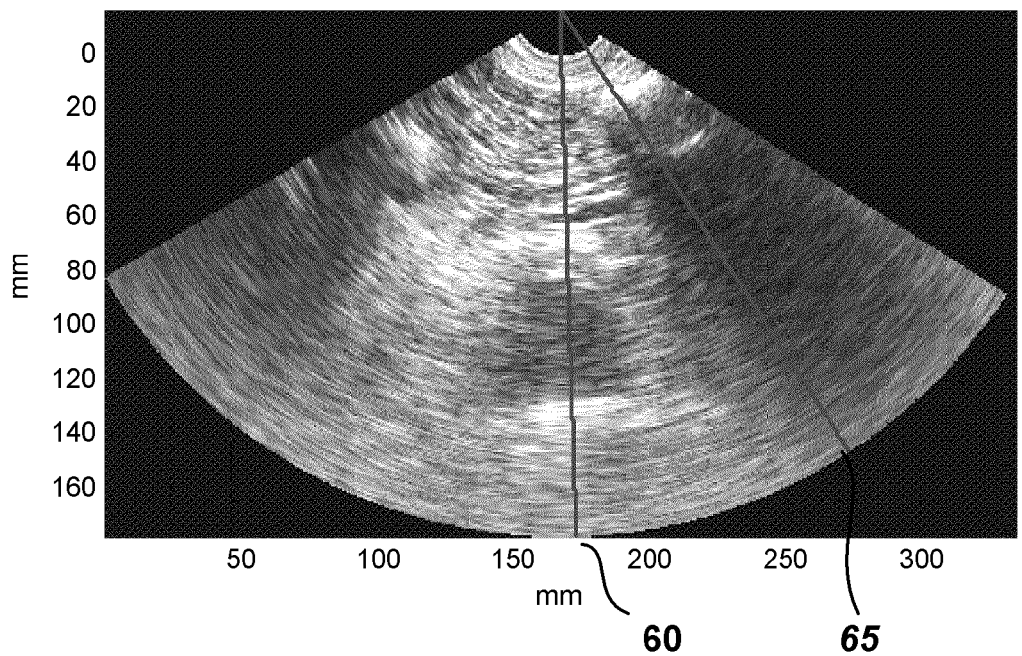
Fig. 6-1
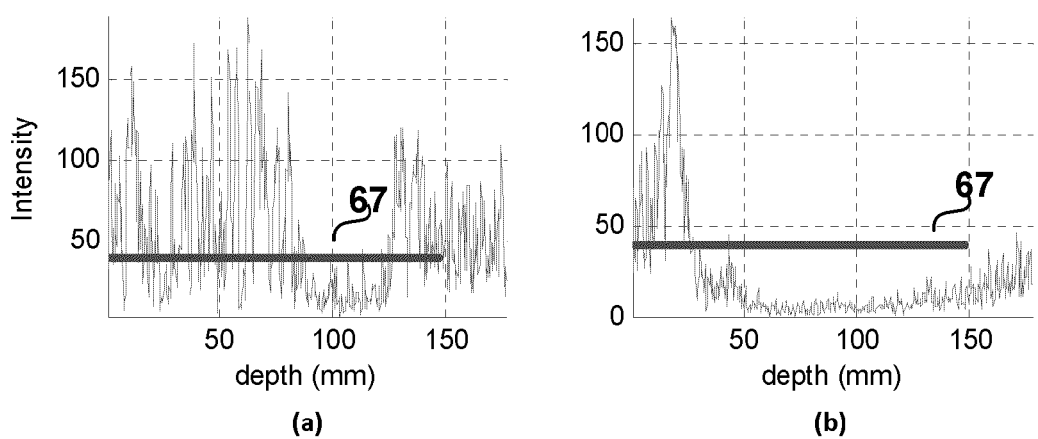
Fig. 6-2
Fig. 6-3

DEVICE, SYSTEM AND METHOD TO MEASURE ABDOMINAL AORTIC ANEURYSM DIAMETER

CROSS REFERENCE TO RELATED APPLICATIONS

This application claims priority to, and incorporates by reference in their entireties, U.S. provisional patent application Ser. No. 61/087,152 filed Aug. 7, 2008 and U.S. provisional patent application Ser. No. 61/094,003 filed Sep. 3, 2008.

This application is also a continuation-in-part of, claims priority to, and incorporates by reference in its entirety U.S. patent application Ser. No. 12/121,721 filed May 15, 2008, which is a continuation-in-part of U.S. patent application Ser. No. 11/968,027 filed Dec. 31, 2007, U.S. patent application Ser. No. 11/926,522 filed Oct. 27, 2007, U.S. patent application Ser. No. 11/925,887 filed Oct. 27, 2007, U.S. patent application Ser. No. 11/925,896 filed Oct. 27, 2007, U.S. patent application Ser. No. 11/925,900 filed Oct. 27, 2007, U.S. patent application Ser. No. 11/925,850 filed Oct. 27, 2007, U.S. patent application Ser. No. 11/925,843 filed Oct. 27, 2007, U.S. patent application Ser. No. 11/925,654 filed Oct. 26, 2007, and U.S. Provisional Patent Application Nos. 60/938,359 filed May 16, 2007; 60/938,371 filed May 16, 2007; and 60/938,446 filed May 16, 2007.

All of the foregoing named applications are incorporated by reference in their entireties as if fully set forth herein.

COPYRIGHT NOTICE

This disclosure is protected under United States and International Copyright Laws. ©2009 Verathon® Incorporated. All Rights Reserved. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The aorta artery in the abdomen carries blood from the heart to the abdominal region. One disorder of the abdominal aorta is known as an abdominal aortic aneurysm, which is a permanent localized dilation of the arterial wall of the abdominal aorta. When dilation of the arterial wall is greater than 1.5 times the typical, i.e. nominal, diameter, it is referred to as an aneurysm. A normal abdominal aorta is shown in FIG. 1-1 (see U.S. Pat. No. 6,905,468). FIG. 1-2 shows a typical aortic aneurysm at. An aortic aneurysm is usually located below the renal arteries and the kidney arteries and above the aorta-iliac bifurcation. Below the aortic-iliac bifurcation are additional arteries. Abdominal aortic aneurysms are a fairly common disorder, occurring in approximately 5-7% of the population over age 60. Since effective screening programs are not yet established, the diagnosis of AAA is frequently made at the time of rupture or impending rupture, which leads to a dramatic increase of post-operative morbidity. (Daly, et al., 2004)

Abdominal aortic aneurysms, depending upon their size, result in pressure on adjacent tissue structure and organs, causing potential embolization and/or thrombosis in those tissues/organs. Rupture of the aneurysm typically results in death, and comprises approximately 2% of all deaths in men over 60 years of age.

Accurate diagnosis of an abdominal aortic aneurysm is important in preventing rupture, as well as in controlling the expansion of the aneurysm. Conventional two-dimension B-mode ultrasound scan devices are currently used to produce measurements of aortic aneurysms, both axially (longitudinally) along the aorta and laterally (radially) across the aorta. Typically, the accuracy is within three millimeters of the actual size of the aneurysm, using conventional CT or MRI processing. These conventional systems, however, are very expensive, both to purchase/lease and to maintain. Further, a trained sonographer is necessary to interpret the results of the scans. As a result, many aneurysms go undetected and/or are not consistently monitored after discovery, until rupture resulting in death of the patient.

A recent prospective study by Vidakovic, et al. (2006) sought to evaluate the diagnostic potential and accuracy in Abdominal Aortic Aneurysm (AAA) screening using an automatic bladder volume indicator (BVI) instrument. The BVI was originally designed for the estimation of post-void residual volumes. The device is inexpensive and can effectively be used after a short training. A measurement method of bladder volume is different between BVI and US, however several reports have found that BVI is as reliable as US to measure post-void residual urine. (Yucel, et al., 2005; Byun, et al., 2003)

In the Vidakovic et al. study AAA volumes were measured in 94 patients, and compared with 2D ultrasound and CT measurement to see if these comparisons can provide a method of screening AAA within certain volume thresholds. The reported results indicated there was an 89% agreement of the diameter measurements by ultrasound (US) as compared with those made with the bladder volume indicator (BVI). Using a cut-off value for the presence of AAA of 50 ml by BVI, the BVI technique predicted AAA with a sensitivity of 94%, a specificity of 82%, a positive predictive value of 88%, and a negative predictive value of 92%. The agreement between standard US and BVI in detecting an AAA was 89%.

This study showed the potential of using the BVI volume. Compared to other portable US devices used to screen patients, the BVI is simpler for use, requires a shorter training period, and is significantly cheaper. One barrier to its adoption is that the current device does not provide automatic conversion values and/or accurate values of AAA diameter. Moreover certain impediments exist to accurate readings of the region of interest that must be overcome for accurate predictive measurements.

Hence, it would be useful to a primary care physician or emergency personnel to have a low-cost device which provides accurate information concerning aortic aneurysms by providing AAA diameter measurements, without the necessity of a trained technician to interpret the scan results. Specifically, the art fails to provide a low cost system, method, and apparatus to automatically and accurately obtain and utilize data derived from an automatic bladder volume instrument (BVI) to provide values of abdominal aortic aneurysm (AAA) diameters.

SUMMARY OF THE INVENTION

An ultrasound transceiver device, system, and method to obtain, analyze, and interpret ultrasonic information from a vascular region of interest to measure the diameter of a suspected blood vessel aneurysm.

BRIEF DESCRIPTION OF THE DRAWINGS

Examples of particular embodiments of the present invention are described in detail below with reference to the following drawings:

FIG. 1-2 shows a typical abdominal aortic aneurysm;

FIGS. 2-1 thru 2-4 depict a partial schematic and a partial isometric view of a transceiver, a scan cone comprising a rotational array of scan planes, and a scan plane of the array of an ultrasound harmonic imaging system;

FIG. 3-1 is a side elevation view of an ultrasound transceiver 10A that includes an inertial reference unit FIG. 3-2 illustrates a side and partial isometric that schematically depicts an ultrasound scanner employing C-mode and B-mode ultrasound modalities;

FIG. 3-3 illustrates a partial isometric and schematic view of an ultrasound scanner system;

FIG. 4 is a schematic illustration of a server-accessed local area network and/or internet in communication with a plurality of ultrasound imaging systems;

FIG. 6-1 is a B-mode image of an AAA is in the same field as a shadow region;

FIGS. 6-2 and 6-3 are histograms of the A-mode lines 65 (FIG. 6-2) and 65 (FIG. 6-3);

FIGS. 7-1 thru 7-12 are twelve B-mode images showing shadows and non-availability;

FIG. 8 schematically illustrates an availability plot in C-mode (view from the top of the scan cone);

FIG. 9-1 and 9-2 illustrates an aiming direction scheme; and a decision tree for the arrow feedback from the indicator 22 of FIG. 3-3;

FIG. 10 illustrates a screen shot of an exemplary aiming guide;

FIG. 11 depicts a flowchart of a aortic aneurysm detection algorithm employing fundamental ultrasound energies;

FIGS. 12-1 and 12-2 are exemplary B-mode images of longitudinal section and cross section of AAA phantom with their typical segmentations (red dotted lines) for volume estimation;

FIGS. 12-3 is a schematic diagram illustrating an exemplary embodiment of the limited segmentation;

DETAILED DESCRIPTION OF THE PARTICULAR EMBODIMENTS

Figures 1, 2:
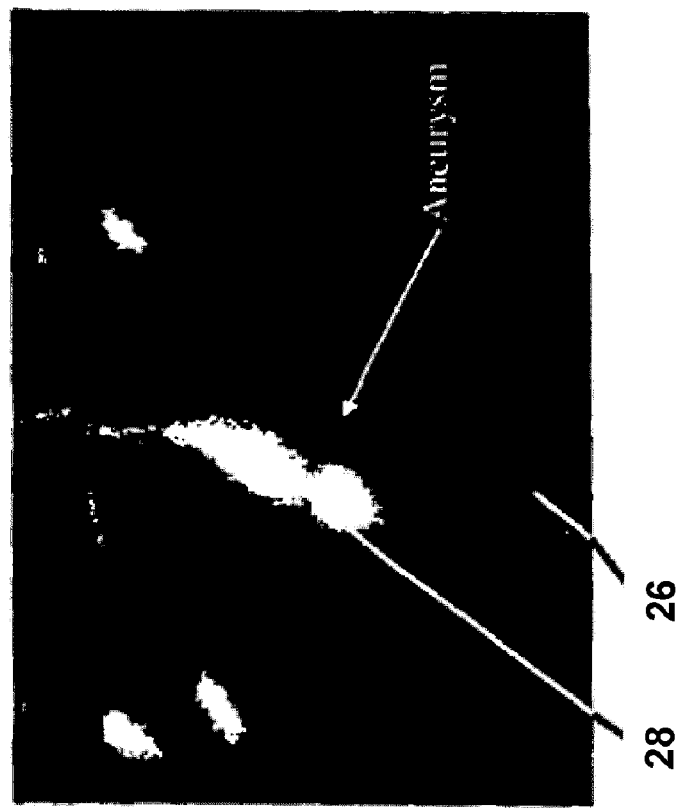
Figure 1:
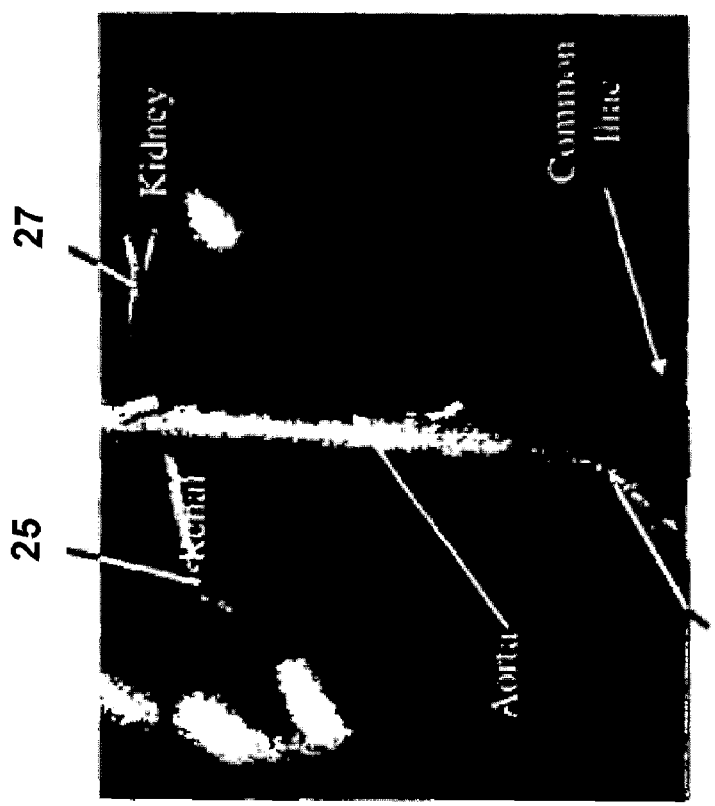
FIG. 1-1 shows a normal abdominal aorta.

Embodiments of the invention may be described in the general context of computer-executable instructions, such as program modules, executed by one or more computer processors or other devices, computer-readable media on which such instructions are stored, and/or the processors/devices themselves. Generally, program modules include routines, programs, objects, components, data structures, etc. that perform particular tasks or implement particular abstract data types. Typically the functionality of the program modules may be combined or distributed as desired in various embodiments.

Embodiments of the invention may include or otherwise utilize at least some form of computer readable media, which may be associated with one or more processors and/or memory devices. Computer readable media can be any available media that can be accessed by one or more components of such operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by one or more components of such operating environment. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

Particular embodiments are described for devices, systems, and corresponding methods encompassing ultrasound detection and the measurement of suspected abdominal aortic aneurysms. The devices, systems, and methods employ transceivers equipped to convey fundamental ultrasound frequencies, and analysis of fundamental echoes returning from a vascular region of interest (ROI). Signal processing algorithms executable by computer systems, described below, are developed to optimally extract information from fundamental ultrasound echoes delivered under A-mode, B-mode, and/or C-mode ultrasound configurations.

Disclosure below includes systems and methods to detect and measure an AAA involving transmitting ultrasound energy having at least one of a fundamental frequency to the AAA, collecting ultrasound echoes returning from the AAA and generating signals from the ultrasound echoes, and identifying within the ultrasound signals those attributable to fundamental ultrasound frequencies. Thereafter, the fundamental-frequency-derived signals undergo signal processing via computer executable program instructions to present an image of the AAA on a display, and calculate the volume and diameter of the AAA.

The signal processing applied to the transceiver echoic fundamental ultrasound signals include an algorithm having computer readable instructions for ascertaining the certainty that a given scan line traverses a AAA, a shadow region, or both a AAA and a shadow region using a grading algorithm for predicting the scan line's AAA or shadow classification.

The ultrasound transceivers or distal collection devices (DCD) are capable of collecting in vivo three-dimensional (3-D) cone-shaped ultrasound images of a patient. During the data collection process initiated by the DCD, a radio frequency pulsed ultrasound field is transmitted into the body, and the back-scattered "echoes" may be transducer-detected and presented as a one-dimensional (1-D) voltage trace, which may be also referred to as a radio frequency (RF) line. After detection of RF signal pulse envelopes, a set of 1-D data samples is interpolated to form a two-dimensional (2-D) image. A plurality of 2-D images can be assembled to form a 3-D ultrasound image.

Particular embodiments described below include a system to detect an abdominal aortic aneurysm. The system includes an ultrasound transceiver positioned to deliver ultrasound energy and receive echoes of the ultrasound energy across a plurality of scan planes; an algorithm configured to signal process the received echoes and characterize detected signals across a plurality of scan planes, wherein a "percentage of availability" measurement may be made. Percentage of availability (POA) may be based on whether relevant information is contained within the scanplane as compared with shadows or other regions not of interest. The system includes a display for presenting a visual depiction of availability contained in a plurality of scan planes; and display for indicating positioning information of the ultrasound transceiver based on the visual depiction of availability.

The BVI9600 Transceiver and Principal of Operation:

FIGS. 2-1-2-4 depict a partial schematic and a partial isometric view of a transceiver, a scan cone comprising a rotational array of scan planes, and a scan plane of the array of various ultrasound systems capable of collecting RF line analysis.

FIG. 2-1 is a side elevation view of an ultrasound transceiver 10A that includes an inertial reference unit 38, according to an embodiment of the invention. The transceiver 10A includes a transceiver housing 35 having an outwardly extending handle 33 suitably configured to allow a user to manipulate the transceiver 10A relative to a patient. Ultrasound transducers operating within the transceiver 10A can be equipped to collect and ready signals for ultrasound fundamental and/or harmonic frequency analysis.

The handle 33 includes a trigger 37 that allows the user to initiate an ultrasound scan of a selected anatomical portion. The transceiver 10A also includes a transceiver dome 34 that contacts a surface portion of the patient when the selected anatomical portion is scanned (See FIG. 5). The dome 34 generally provides an appropriate acoustical impedance match to the anatomical portion and/or permits ultrasound energy to be properly focused as it is projected into the anatomical portion. The transceiver 10A further includes one transducer element, or preferably an array of separately excitable ultrasound transducer elements, positioned within or otherwise adjacent to the housing 35. The transducer elements can be suitably positioned within the housing 35 or otherwise to project ultrasound energy outwardly from the dome 34, and to permit reception of acoustic reflections generated by internal structures within the anatomical portion. The one or more array of ultrasound elements can include a one-dimensional, or a two-dimensional array of piezoelectric elements that can be moved within the housing 35 by a motor. Alternatively, the array can be stationary with respect to the housing 35 so that the selected anatomical region can be scanned by selectively energizing the elements in the array.

In one embodiment of the transceiver 10A, a directional indicator panel or aiming guide panel 32 includes a plurality of arrows that can be illuminated for initial targeting and guiding a user to access the targeting of an organ or structure within a region of interest (ROI).

In the BVI 9600 system 70 described in FIG. 3-3 below, the directional indicator panel 32 of transceiver 10A has a virtual equivalent in the form of a targeting icon screenshot 77B that appears on an display 76 on the console 74; both the indicator panel 32 and display 76 (displaying targeting icon 77B) can function to guide a transceiver user to place the transceiver to obtain a "good scan" of the abdominal aortic region of interest (e.g., for the detection of AAA).

In particular embodiments, if the AAA structure is centered (as indicated by reference numeral 77C), and there are no impediments to the scanlines, e.g., shadows caused by air pockets (see discussion below) from placement of the transceiver 10A or 10C acoustically placed against the dermal surface at a first location of the subject, the directional arrows will be not illuminated. If the AAA is off-center or a shadow appears in the field of interest, an arrow or set of arrows can be illuminated to direct the user to reposition the transceiver 10A, 10C acoustically at a second or subsequent dermal location of the subject. The acoustic coupling can be achieved by liquid sonic gel applied to the skin of the patient or by sonic gel pads against which the transceiver dome 34 is placed. The directional indicator panel 32 can also be presented on the display 54 of computer 52 in imaging subsystems described in FIG. 4 below, and/or presented on the transceiver display 36.

Turning back to FIG. 2.1, transceiver 10A can, in one embodiment, include an inertial reference unit that includes an accelerometer and/or gyroscope 38 positioned preferably within or adjacent to housing 35. The accelerometer 38 can be operable to sense an acceleration of the transceiver 10A, preferably relative to a coordinate system, while the gyroscope can be operable to sense an angular velocity of the transceiver 10A relative to the same or another coordinate system. Accordingly, the gyroscope can be of conventional configuration that employs dynamic elements, or it can be an optoelectronic device, such as the known optical ring gyroscope. In one embodiment, the accelerometer and the gyroscope can include a commonly packaged and/or solid-state device. One suitable commonly packaged device can be the MT6 miniature inertial measurement unit, available from Omni Instruments, Incorporated, although other suitable alternatives exist. In other embodiments, the accelerometer and/or the gyroscope can include commonly packaged microelectromechanical system (MEMS) devices, which are commercially available from MEMSense, Incorporated. As described in greater detail below, the accelerometer and the gyroscope cooperatively permit the determination of positional and/or angular changes relative to a known position that is proximate to an anatomical region of interest in the patient. Other configurations related to the accelerometer and gyroscope concerning transceivers 10A, 10B, 10C of FIGS. 2.-1, 3-2, and/or 3-3 equipped with inertial reference units and the operations thereof are described in co-pending U.S. patent application Ser. No. 11/222,360 filed Sep. 8, 2005, herein incorporated by reference.

Figures 1, 3:
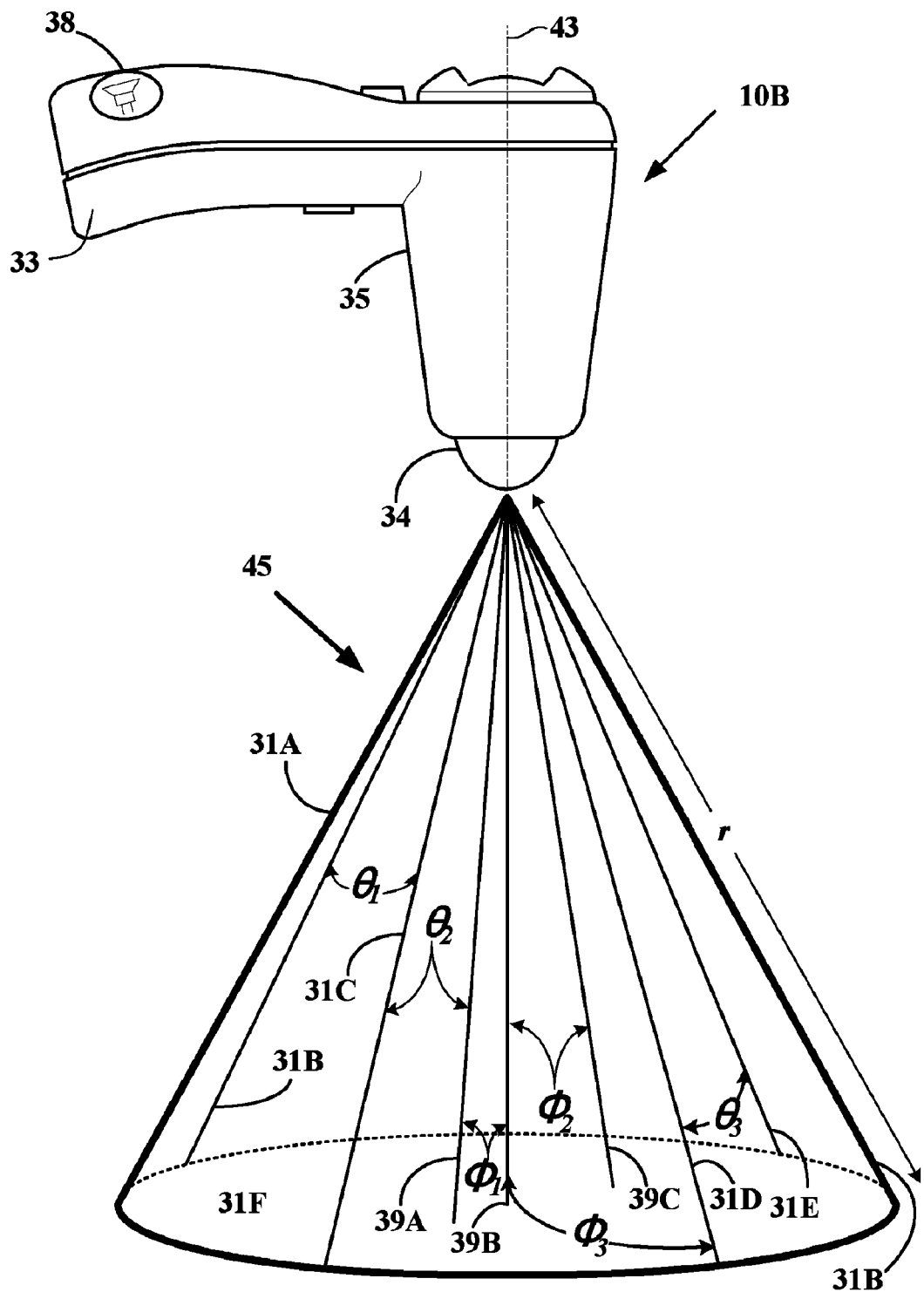
Figures 2, 3:
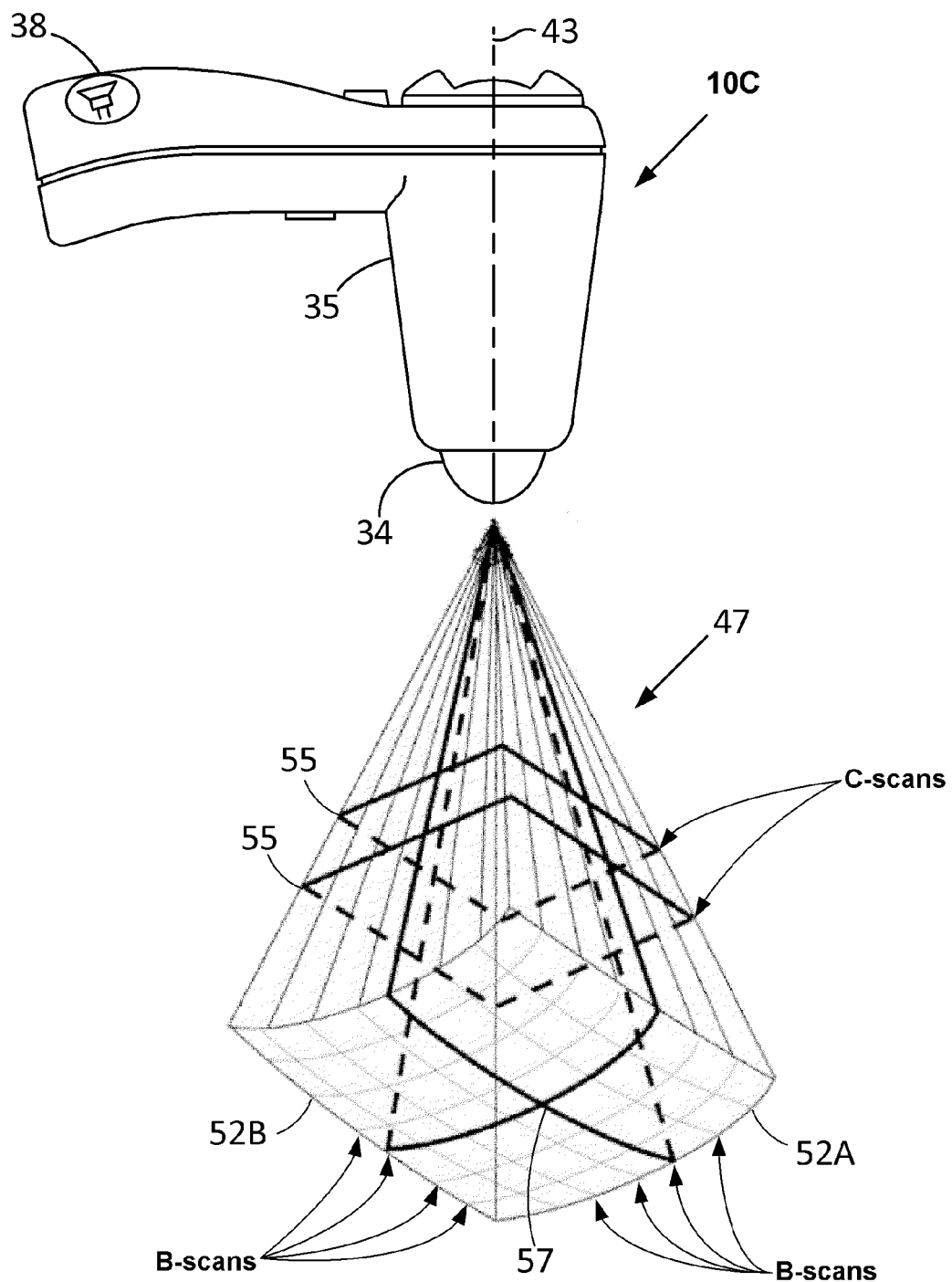
Figure 3:
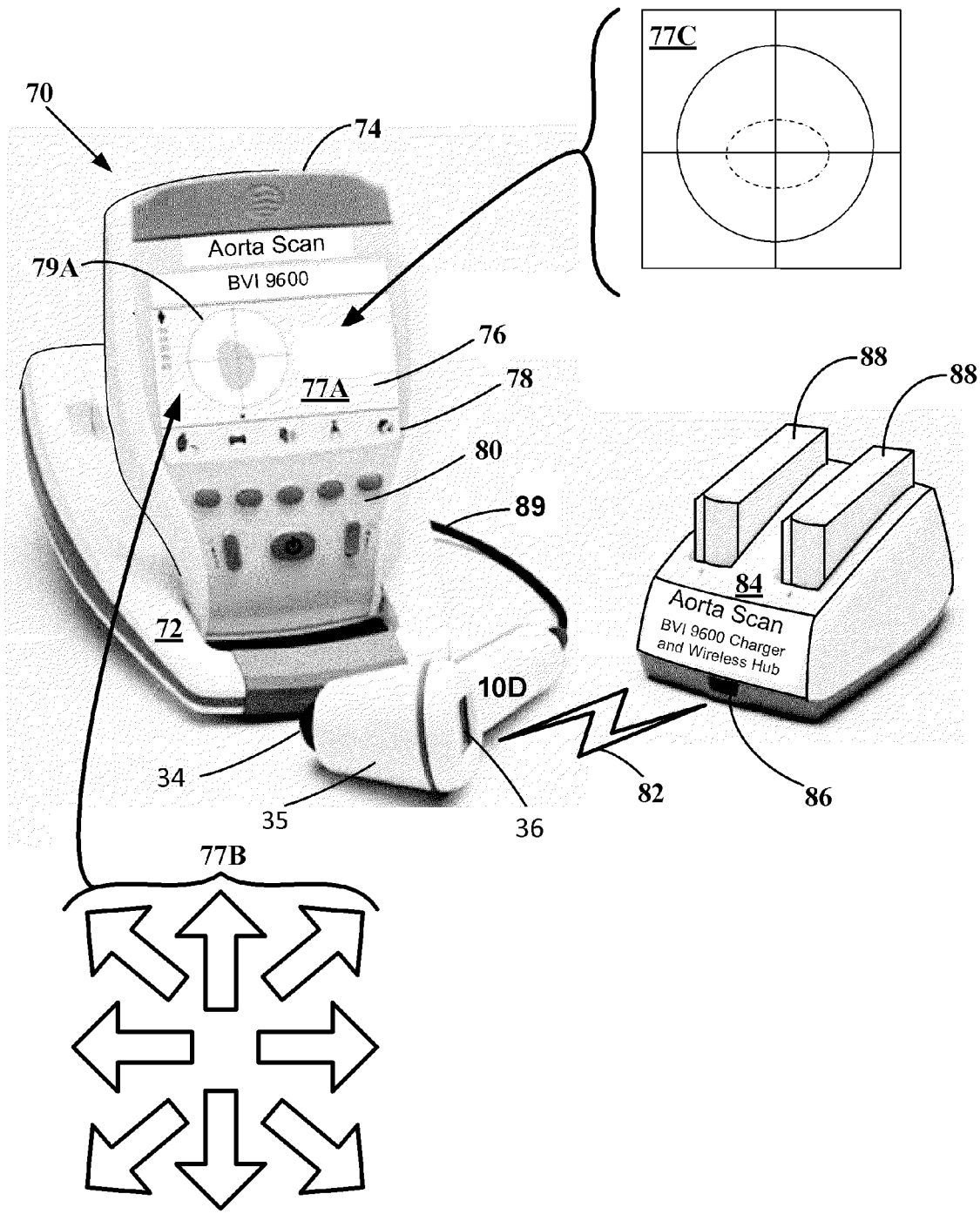
Figure 4:
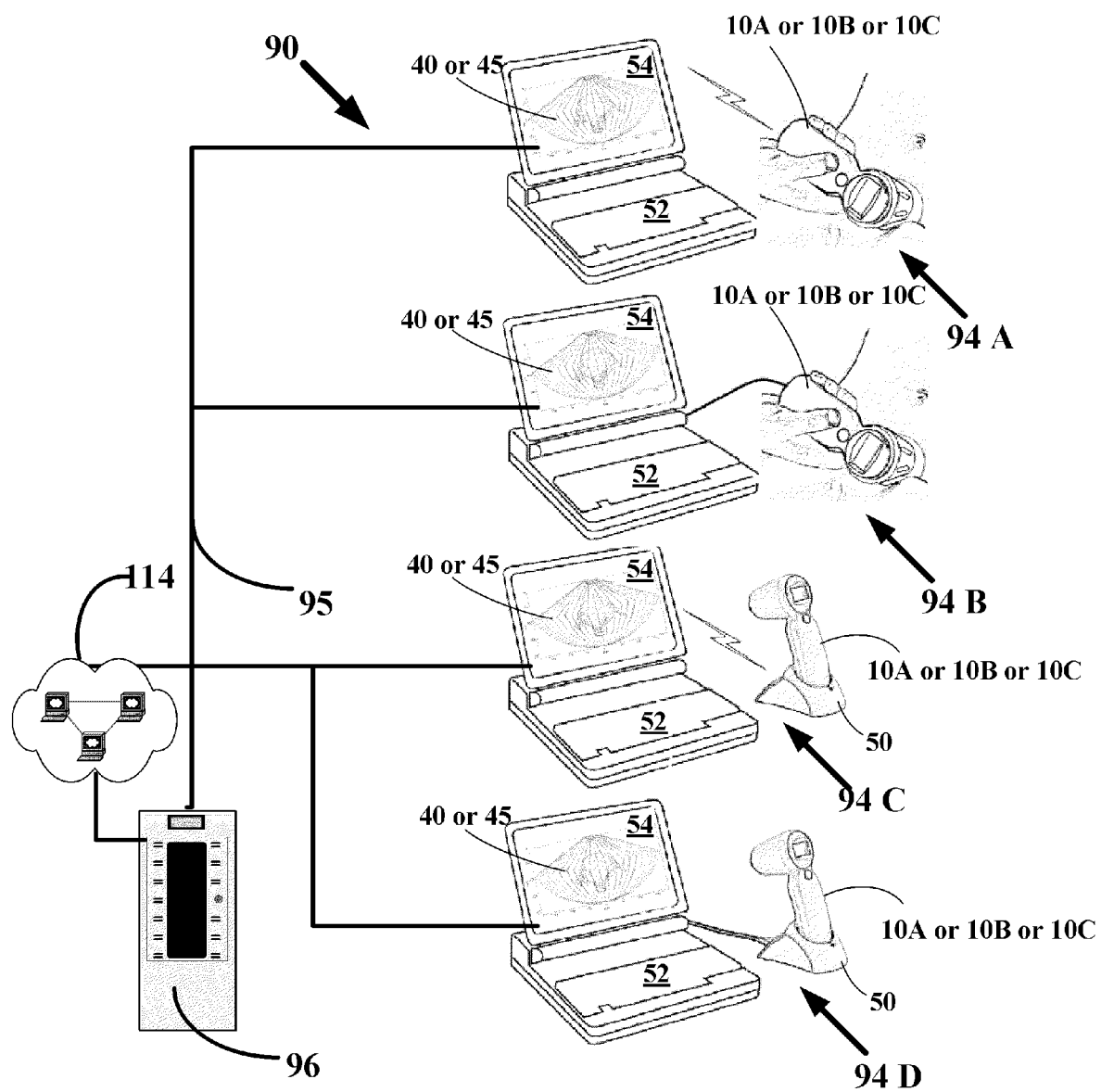

The transceiver 10A shown in FIG. 2-1 includes a display 36 and/or is capable of being in signal communication with a device with a display, FIGS. 3-3 and 4) operable to allow viewing of processed results from an ultrasound scan, and/or to allow an operational interaction between the user and the transceiver 10A. For example, the display 36 of the handheld transceiver 10A can be configured to display alphanumeric data that indicates a proper and/or an optimal position of the transceiver 10A relative to the selected anatomical portion. Display 36 can be used to view two- or three-dimensional images of the selected anatomical region. Accordingly, the display 36 can be a liquid crystal display (LCD), a light emitting diode (LED) display, a cathode ray tube (CRT) display, or other suitable display devices operable to present alphanumeric data and/or graphical images to a user.

In operation, to scan a selected anatomical portion of a patient, the transceiver dome 34 of the transceiver 10A can be positioned against a surface portion of a patient that is proximal to the anatomical portion to be scanned. See for example FIG. 5 for exemplary positioning for AAA detection. The user actuates the transceiver 10A by depressing a trigger 37. In response, the transceiver 10A transmits ultrasound signals into the body, and receives corresponding return echo signals that can be at least partially processed by the transceiver 10A to generate an ultrasound image of the selected anatomical portion. In a particular embodiment, the transceiver 10A transmits ultrasound signals in a range that extends from approximately about two megahertz (MHz) to approximately about ten MHz. Ultrasound energies beyond 10 MHz can be utilized.

In one embodiment, the transceiver 10A can be operably coupled to an ultrasound system that can be configured to generate ultrasound energy at a predetermined frequency and/or pulse repetition rate and to transfer the ultrasound energy to the transceiver 10A. The system also includes a processor that can be configured to process reflected ultrasound energy that is received by the transceiver 10A to produce an image of the scanned anatomical region. As discussed, the system generally includes a viewing device, such as a cathode ray tube (CRT), a liquid crystal display (LCD), a plasma display device, or other similar display device, that can be used to view the generated image. The system can also include one or more peripheral devices that cooperatively assist the processor to control the operation of the transceiver 10A, such a keyboard, a pointing device, or other similar devices. In still another particular embodiment, the transceiver 10A can be a self-contained device that includes a microprocessor positioned within the housing 35 and software associated with the microprocessor to operably control the transceiver 10A, and to process the reflected ultrasound energy to generate the ultrasound image. Accordingly, the display 36 can be used to display the generated image and/or to view other information associated with the operation of the transceiver 10A. For example, the information can include alphanumeric data that indicates a preferred position of the transceiver 10A prior to performing a series of scans.

In yet another particular embodiment, the transceiver 10A can be operably coupled to a general-purpose computer (see FIG. 4), such as a laptop or a desktop computer that includes software that at least partially controls the operation of the transceiver 10A, and also includes software to process information transferred from the transceiver 10A, so that an image of the scanned anatomical region can be generated. The transceiver 10A can also be optionally equipped with electrical contacts to make communication with receiving cradles 50 as illustrated in FIG. 4 below. Although transceiver 10A of FIG. 2-1 can be used in any of the foregoing embodiments, other transceivers can also be used. For example, the transceiver can lack one or more features of the transceiver 10A. For example, a suitable transceiver need not be a manually portable device, and/or need not have a top-mounted display, and/or can selectively lack other features or exhibit further differences.

FIG. 2-2 is a graphical representation of a plurality of scan planes that form a three-dimensional (3D) array having a substantially conical shape. An ultrasound scan cone 40 formed by a rotational array of two-dimensional scan planes 42 projects outwardly from the dome 34 of the transceivers 10A. Other transceiver embodiments of transceiver 10A can also be configured to develop a scan cone 40 formed by a rotational array of two-dimensional scan planes 42. The pluralities of scan planes 40 can be oriented about an axis 43 extending through the transceivers 10A. One or more, or preferably each of the scan planes 42 can be positioned about the axis 43, preferably, but not necessarily at a predetermined angular position θ. The scan planes 42 can be mutually spaced apart by angles $\theta_1$ and $\theta_2$. Correspondingly, the scan lines within each of the scan planes 42 can be spaced apart by angles $\phi_1$ and $\phi_2$. Although the angles $\theta_1$ and $\theta_2$ are depicted as approximately equal, it is understood that the angles $\theta_1$ and $\theta_2$ can have different values. Similarly, although the angles $\phi_1$ and $\phi_2$ are shown as approximately equal, the angles $\phi_1$ and $\phi_2$ can also have different values. Other scan cone configurations are possible. For example, a wedge-shaped scan cone, or other similar shapes can be generated by the transceiver 10A.

FIG. 2-3 is a graphical representation of a scan plane 42. The scan plane 42 includes the peripheral scan lines 44 and 46, and an internal scan line 48 having a length r that extends outwardly from the transceiver 10A. Thus, a selected point along the peripheral scan lines 44 and 46 and the internal scan line 48 can be defined with reference to the distance r and angular coordinate values $\phi$ and $\theta$. The length r preferably extends to approximately 18 to 20 centimeters (cm), although any length is possible. Particular embodiments include approximately seventy-seven scan lines 48 that extend outwardly from the dome 34, although any number of scan lines is possible.

As described above, the angular movement of the transducer can be mechanically effected and/or it can be electronically or otherwise generated. In either case, the number of lines 48 and the length of the lines can vary, so that the tilt angle $\phi$ sweeps through angles approximately between −60° and +60° for a total arc of approximately 120°. In one particular embodiment, the transceiver 10A can be configured to generate approximately seventy-seven scan lines between the first limiting scan line 44 and a second limiting scan line 46. In another particular embodiment, each of the scan lines has a length of approximately 18 to 20 centimeters (cm). The angular separation between adjacent scan lines 48 (FIG. 2-2) can be uniform or non-uniform. For example, and in another particular embodiment, the angular separation $\phi_1$ and $\phi_2$ (as shown in FIG. 2-3) can be about 1.5°. Alternately, and in another particular embodiment, the angular separation $\phi_1$ and $\phi_2$ can be a sequence wherein adjacent angles can be ordered to include angles of 1.5°, 6.8°, 15.5°, 7.2°, and so on, where a 1.5° separation is between a first scan line and a second scan line, a 6.8° separation is between the second scan line and a third scan line, a 15.5° separation is between the third scan line and a fourth scan line, a 7.2° separation is between the fourth scan line and a fifth scan line, and so on. The angular separation between adjacent scan lines can also be a combination of uniform and non-uniform angular spacings, for example, a sequence of angles can be ordered to include 1.5°, 1.5°, 1.5°, 7.2°, 14.30, 20.2°, 8.0°, 8.0°, 8.0°, 4.3°, 7.8°, and so on.

FIG. 2-4 is a graphical representation of a plurality of scan lines emanating from the hand-held ultrasound transceiver 10A forming a single scan plane 42 extending through a cross-section of a section of the abdominal aorta 51. The number and location of the internal scan lines emanating from the transceiver 10A within a given scan plane 42 can thus be distributed at different positional coordinates about the axis line 11 as can be required to sufficiently visualize structures or images within the scan plane 42. As shown, four portions of off-centered shadow regions 49 are exhibited as irregular regions and a cross section of the abdominal aorta 51 region of interest (ROI) is depicted as in the center. Three portions can be viewable within the scan plane 42 in totality, and one can be truncated by the peripheral scan line 44.

FIG. 3-1 depicts a partial schematic and partial isometric and side view of transceiver 10B, and a scan cone array comprised of 3D-distributed scan lines in an alternate embodiment of an ultrasound system. A plurality of three-dimensional (3D) distributed scan lines emanating from a transceiver that cooperatively forms a scan cone 45. Each of the scan lines has a length r that projects outwardly from the transceiver 10B of FIGS. 2-1-2-4. As illustrated, the transceiver 10B emits 3D-distributed scan lines within the scan cone 30 that can be one-dimensional ultrasound A-lines. Other transceiver embodiments can also be configured to emit 3D-distributed scan lines. Taken as an aggregate, these 3D-distributed A-lines define the conical shape of the scan cone 45. The ultrasound scan cone 45 extends outwardly from the dome 34 of the transceiver 10B centered about an axis line 43. The 3D-distributed scan lines of the scan cone 43 include a plurality of internal and peripheral scan lines that can be distributed within a volume defined by a perimeter of the scan cone 43. Accordingly, the peripheral scan lines 31A-31F define an outer surface of the scan cone 45, while the internal scan lines 39A-39C can be distributed between the respective peripheral scan lines 31A-31F. Scan line 39B can be generally collinear with the axis 43, and the scan cone 45 can be generally and coaxially centered on the axis line 43.

The locations of the internal and peripheral scan lines can be further defined by an angular spacing from the center scan line 39B and between internal and peripheral scan lines. The angular spacing between scan line 39B and peripheral or internal scan lines can be designated by angle $\Phi$ and angular spacings between internal or peripheral scan lines can be designated by angle $\emptyset$. The angles $\Phi_1$, $\Phi_2$, and $\Phi_3$ respectively define the angular spacings from scan line 39B to scan lines 39A, 39C, and 31D. Similarly, angles $\emptyset_1$, $\emptyset_2$, and $\emptyset_3$ respectively define the angular spacings between scan line 31B and 31C, 31C and 39A, and 31D and 31E.

With continued reference to FIG. 3-1, the plurality of peripheral scan lines 31A-E and the plurality of internal scan lines 39A-D can be three dimensionally distributed A-lines (scan lines) that are not necessarily confined within a scan plane, but instead can sweep throughout the internal regions and along the periphery of the scan cone 45. Thus, a given point within the scan cone 45 can be identified by the coordinates r, $\Phi$, and $\emptyset$ whose values generally vary. The number and location of the internal scan lines emanating from the transceiver 10B can thus be distributed within the scan cone 45 at different positional coordinates as required to sufficiently visualize structures or images within a region of interest (ROI) in a patient. The angular movement of the ultrasound transducer within the transceiver 10B can be mechanically effected, and/or it can be electronically generated. In any case, the number of lines and the length of the lines can be uniform or otherwise vary, so that angle $\Phi$ sweeps through angles approximately between −60° between scan line 39B and 31A, and +60° between scan line 39B and 31B. Thus angle $\Phi$ in this example presents a total arc of approximately 120°.

In one embodiment, the transceiver 10B can be configured to generate a plurality of 3D-distributed scan lines within the scan cone 45 having a length r, in one embodiment for example, of approximately 20 to 40 centimeters (cm).

FIG. 3-2 illustrates a transceiver 10C configured with a transducer designed to provide a fan-like (e.g., having planar sides) conic scan cone 47 utilizing C-mode and B-mode ultrasound modalities. The transceiver 10C projects a series of B-mode scan planes 52A and 52B that oscillate like a pendulum between extremes within the scan cone 47. The B-mode scan planes 52A, 52B may be derived from a plurality of scan lines similar to scan lines 44, 46, and 48 of FIGS. 2-3 and 2-4. The pendulum oscillating scan planes 52A and 52B can be arranged substantially at right angles to each other as depicted at axis crossing 57. The oscillating scan planes 52A and/or 52B can define a series of C-scan planes 55 that vary in depth location from the transceiver dome 34. The C-scan planes 55 move from the transducer vanishing point, and the B-scan planes angularly radiate from the transducer vanishing point. For transceiver 10C users, a portion of the abdominal aorta taken as a C-mode shape is displayed on the transceiver display 16. The C-scan geometry shown as scan planes 55 present a substantially square-like ultrasound area within the scan cone 47. The C-Scan image information contained within scan planes 55 presents a cross-section view of the ultrasound at a particular depth probed by the transceiver 10C. The C-mode may be more representative of a portion of the abdominal aorta than the actual whole of the length of the aorta. In this depiction, the C-Scan illustrates a cross-section view of the ultrasound at a particular depth to obtain a targeting image of the abdominal aorta. The targeting image may be more of a binary image showing the lines and spaces that are inside the aorta versus those that are outside of the aorta. The definition of C-mode image basically may be a plane parallel to the face of the transducer to obtain a projection image of the AAA region. The C-mode acquired projection image can yield abdominal aorta information not confined to simply one a single plane parallel to the transducer surface, but multiple planes denoted as C-scans. In the transceives substantially similar to the BVI9600 transceiver product, the C-mode acquired projection image may be binary, and can include a non-AAA region and an AAA region. The AAA region may be presented as an interpolated shape that may be generated from one side to the opposite side, for example the left most and the right most sides of a valid segmentation, or cut, the AAA region on all planes.

FIG. 3-3 illustrates a partial isometric and schematic view of an ultrasound AAA detection system 70 utilizing a transceiver probe 10D and console 74 combination. The AAA detection system 70 may be battery powered and portable and can also be referred to as the BVI9600 with AortaScreen Mode system. Other embodiments can include line power. The ultrasound transceiver 10D may be configured to send out and receive ultrasound RF signals. The received RF may be transmitted to console 74. The DSP in console can process the RF information to extract the information relevant to the detected feature of each line. Each line is classified as being "available" or "non-available", as will be described below, based on a set threshold value. The classification of information contained in each scanline can be integrated with the image processing module for accurate and optimal positioning of the transceiver for segmentation and volume measurement.

The transceiver 10D can have a transceiver display 36, housing 35 and dome 34 design similar to transceivers 10A and 10B, and may be in signal communication to console 74 via signal cable 89. The console 74 can be pivoted from console base 72. The console 74 includes a display 76, detection and operation function panel 78, and select panel 80. The detection and operation function provide for targeting the abdominal aorta, allow user voice annotation recording, retrieval and playback of previously recorded voice annotation files, and current and previously stored 3D and 2D scans.

As illustrated in FIG. 3-3, display 76 provides a screenshot 77C with a targeting icon 79A including cross hairs centered in a cross sectional depiction of an abdominal aorta. Other screen shots can appear in the display 76 depending on which function key is pressed in the function panel 78. A targeting icon screenshot 77B with a plurality of directional arrows can appear and flash to guide the user to move the transceiver 10C to center the abdominal aorta or AAA. The targeting icon screenshot 77B can also appear on the display 36 of the transceiver 10D. The targeting icon screenshot 77B similarly guides the user to place the transceiver 10D to center the abdominal aorta or AAA or other region of interest as the directional indicator panel 32 did in transceiver 10A of FIG. 2-1 above.

As illustrated in FIG. 3-3, the transceiver 10D can be in wireless communication via wireless signal 82 with the wireless hub 84; the output from the transceiver 10D can be delivered to a wireless hub 84 via wireless signal port 86. The wireless hub 84 can also charge batteries 88 for loading into the battery compartment (not shown) of console 74. In one embodiment, all the calculations can be performed in the imaging console 74. The BVI9600-embodiment system 70 does not require a computer or network to complete the analysis and imaging processing. In other embodiments, the system 70 can utilize the wireless hub 84 as a gateway to transmit transceiver 10D acquired imaging information in local and Internet systems similar to that described in FIG. 4 below.

FIG. 4 is a schematic illustration of a server-accessed local area network and/or an internet system in communication with a plurality of ultrasound imaging systems. In an exemplary embodiment, an ultrasound system 90 can include one or more personal computer devices 52 that can be coupled to a server 96 by a communications system 95. The devices 52 can be, in turn, coupled to one or more ultrasound transceivers 10A and/or 10B and/or 10C, for examples the ultrasound sub-systems 94A-94D. Ultrasound based images of organs or other regions of interest derived from either the signals of echoes from fundamental frequency ultrasound thereof, can be shown within scan cone 40 or 45 presented on display 54. The server 96 can be operable to provide additional processing of ultrasound information, or it can be coupled to still other servers (not shown in FIG. 4) and devices. Transceivers 10A/B/C can be in wireless communication with computer 52 in sub-system 94A, in wired signal communication in sub-system 94B, in wireless communication with computer 52 via receiving cradle 50 in sub-system 94C, or in wired communication with computer 52 via receiving cradle 50 in sub-system 94D.

An Internet system 114 can be coupled or otherwise in communication with the ultrasound sub-systems 94A-94D.

Scanning and Placement of Transceiver and Determination of "Availability":

During the field evaluation of AAA scan-mode, a 2D real time ultrasound instrument was determined to be preferably equipped to find optimal scan locations by searching the interested area with realtime B-mode image feedback. The BVI9600 model has been optimized to inform a user whether a 3D data set is valid or not, prior to collection of useful data. This was not a capability of the previous BVI6500 AAA mode, where only one B-mode image (cross section of an aorta) was provided for a user review after the 3D scan was completed. The BVI6500 B-mode image did not represent the 3D data set condition.

In contrast, the BVI9600 of the present invention investigates each scanline to determine whether the scanline contains any object information relevant to the region of interest or is just shadow blocked by air pocket. In the case that the scanline has any object information, it may be called "Available". By plotting these availabilities in the aiming screen in real-time and guiding a user with aiming arrow, the user can avoid the air blocked scan.

Figure 5:
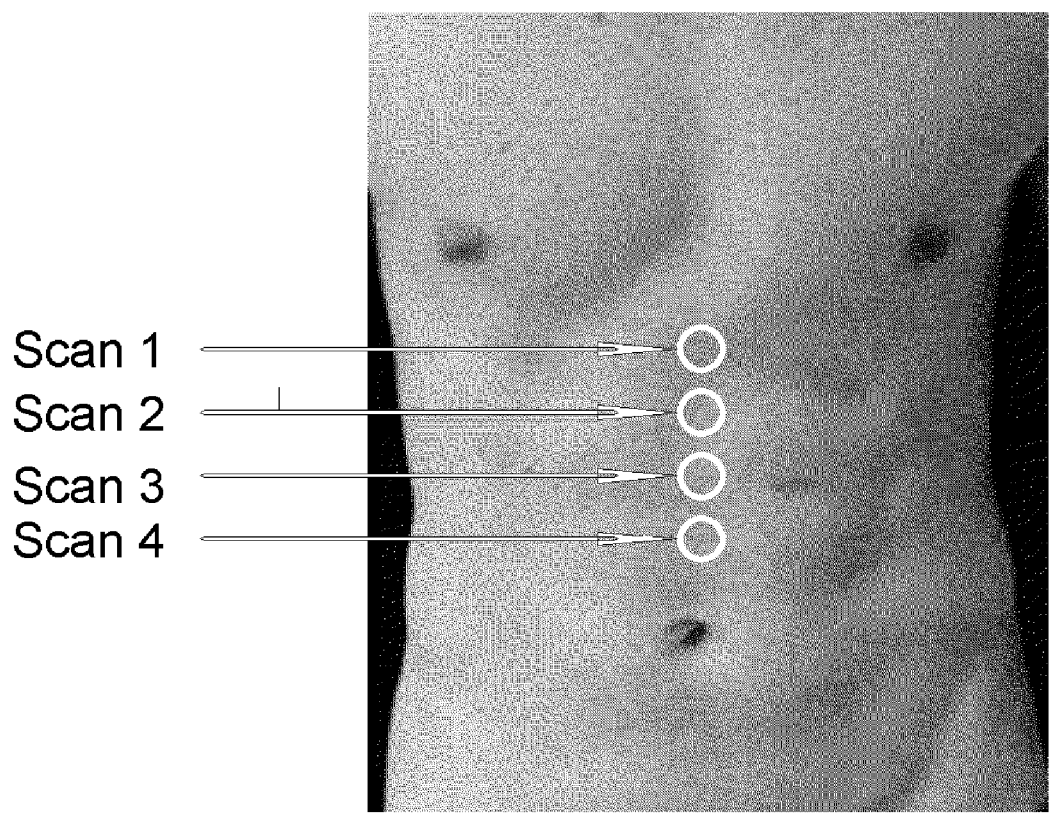
FIG. 5 shows exemplary probe locations along the midline of a patient's torso.

Referring now to FIG. 5, a plurality of measurements along a patient's midline may be taken to find the maximal measurement of the abdominal aorta. In operation, gel may be applied at the midline of the body approximately 1 inch (2.5 cm) below the xiphoid (sternum); making sure that there is enough gel to cover the probe head 34. FIG. 5 shows four such exemplary scan probe locations along the midline of a patient's torso. Firm pressure may be applied, noting that patients with excess tissue can require more pressure in order to obtain a good quality scan. The trigger/scan button 37 of the transceiver 10A, for example, may be then depressed. An aim/scan screen appears, for example in display 36 of the transceiver (FIG. 2.1) and/or display 76 on consol 74 and the instrument performs a 3D scan of the patient's region of interest (ROI).

Figures 1, 7, 8, 9, 10, 11, 12:
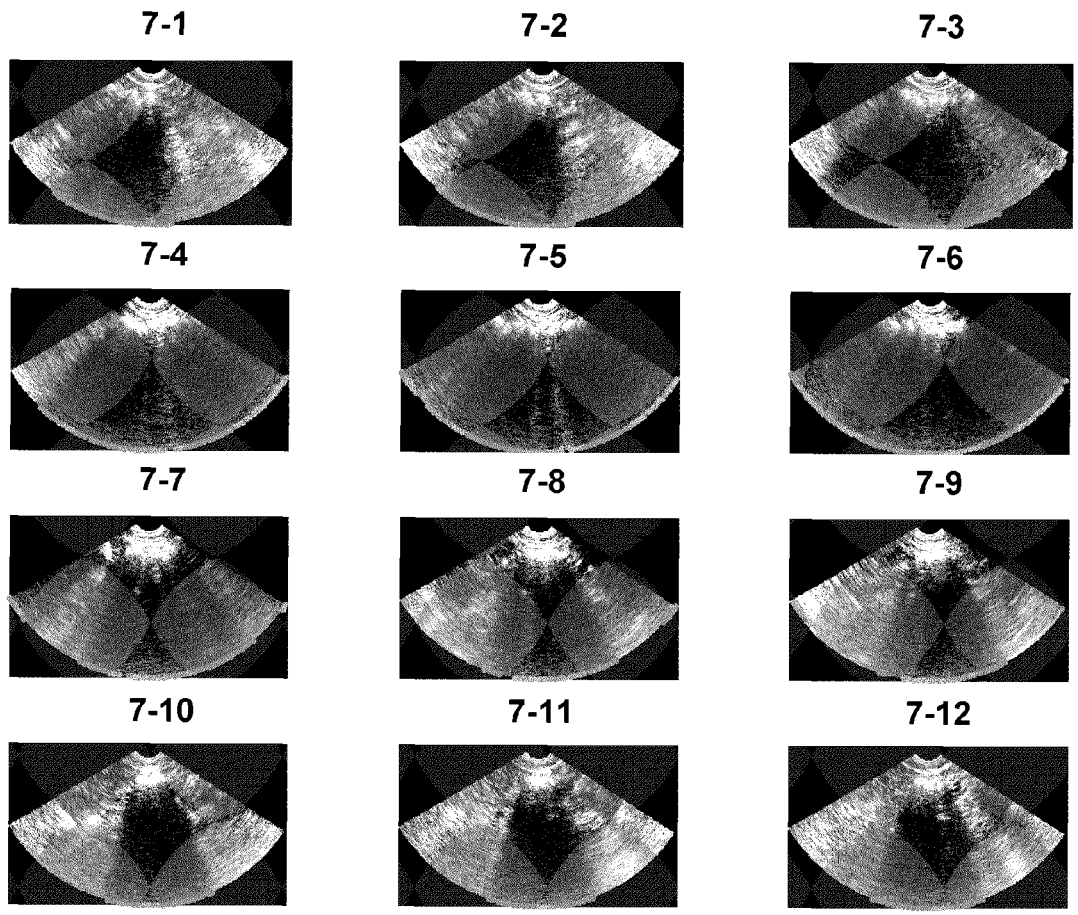
Figure 8:
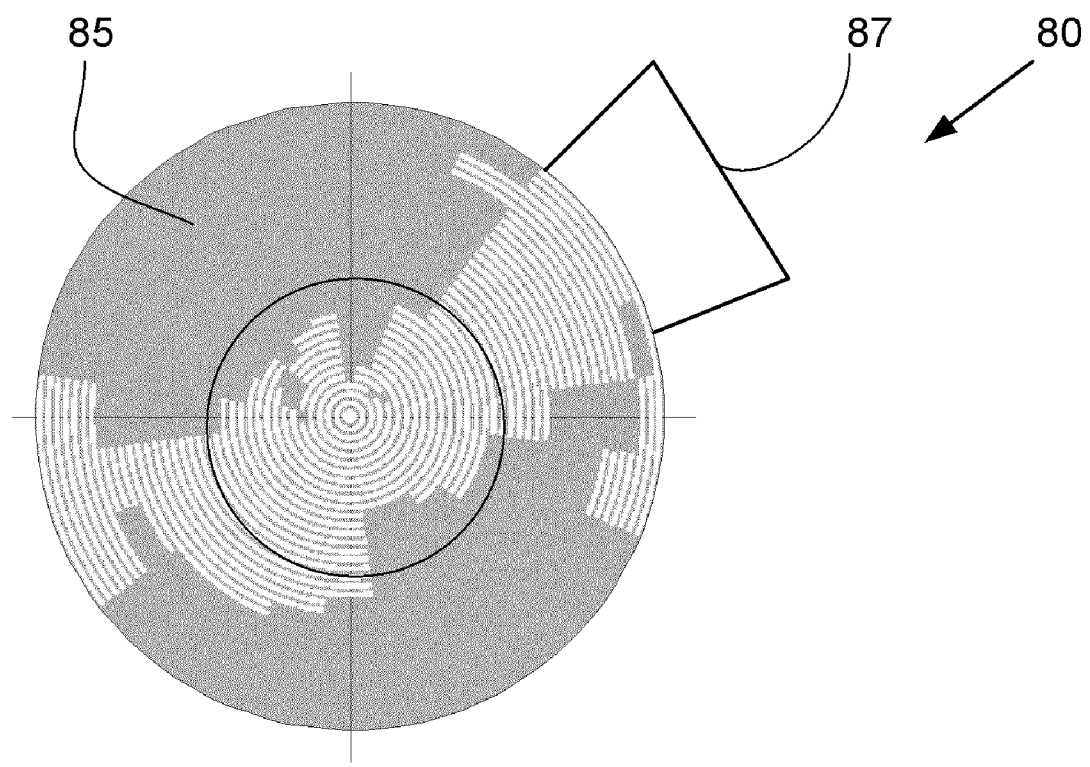
Figures 1, 9:
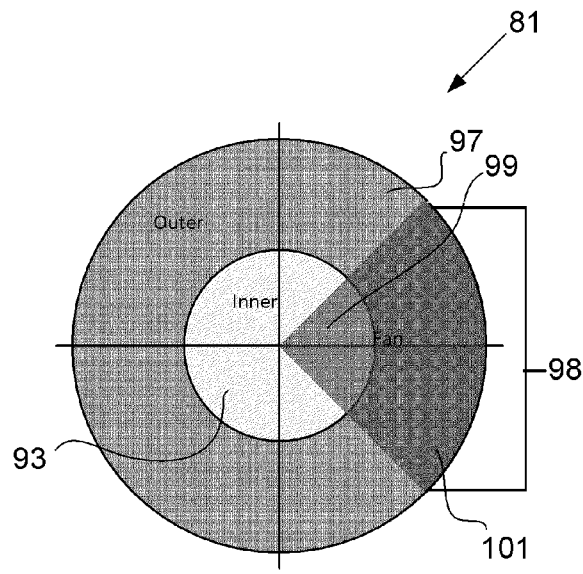
Figures 2, 9:
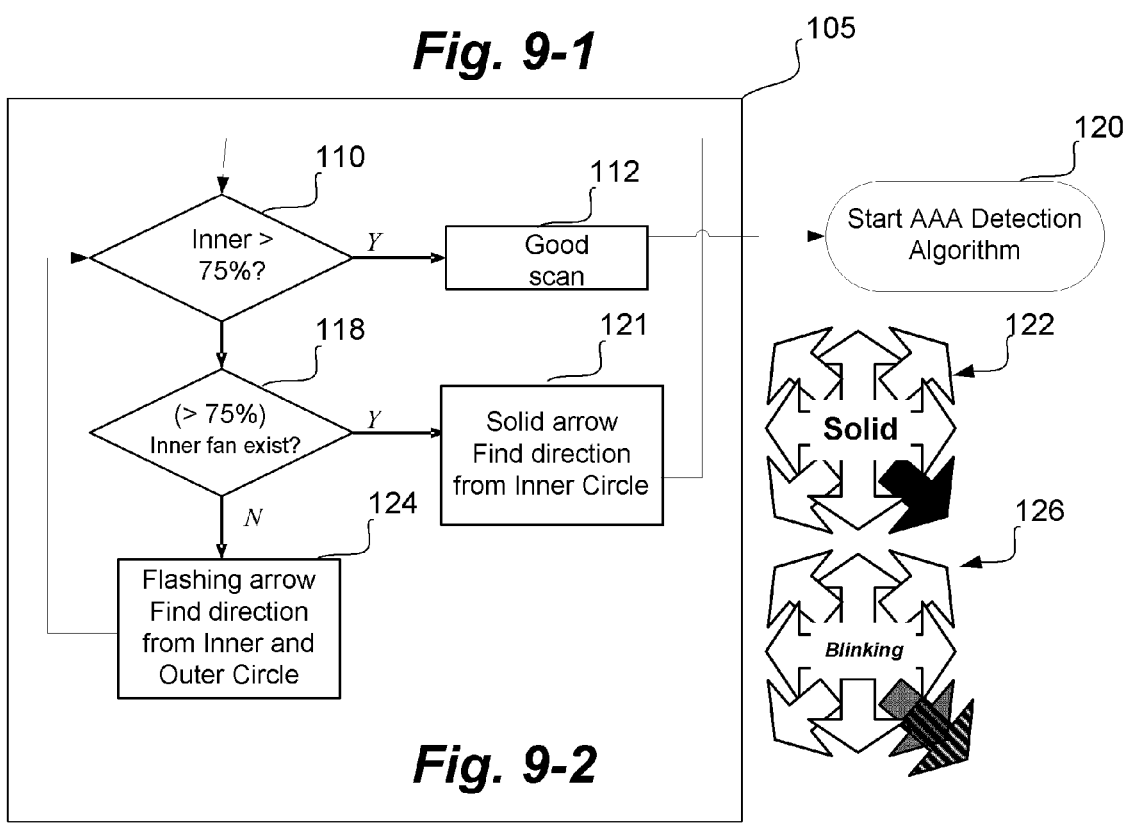
Figure 10:
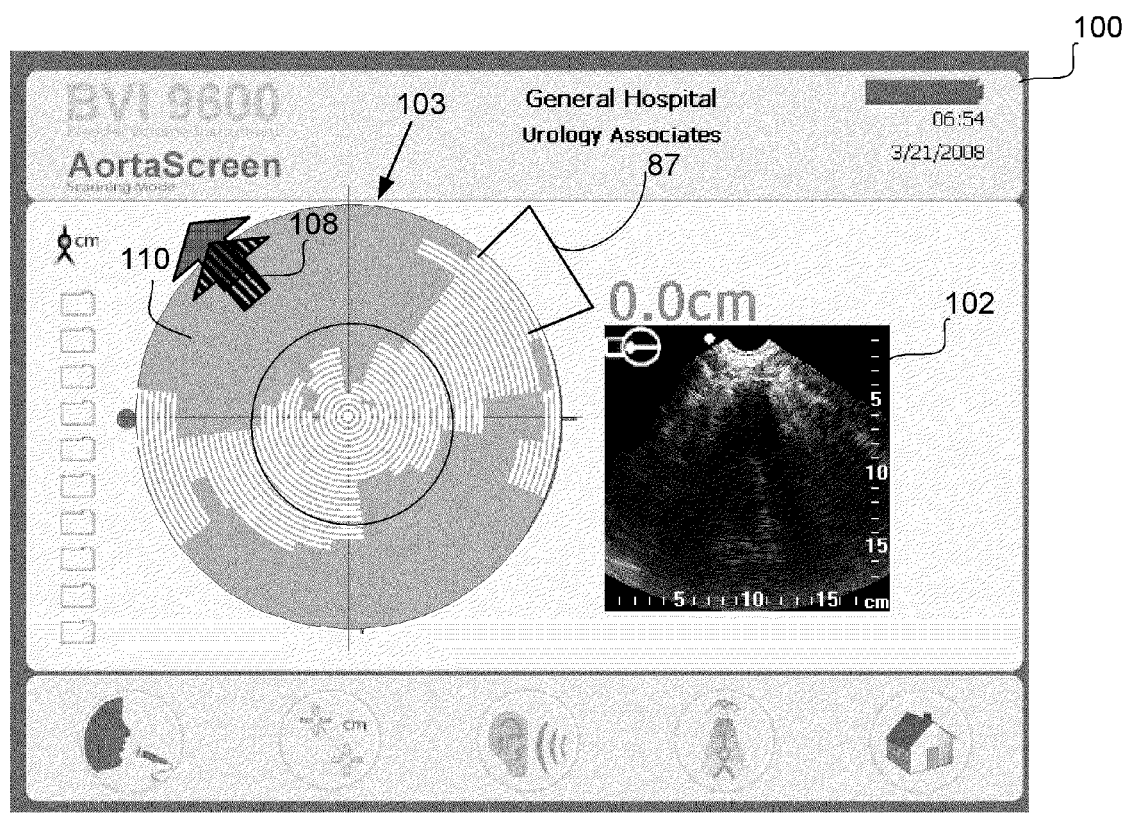
Figure 11:
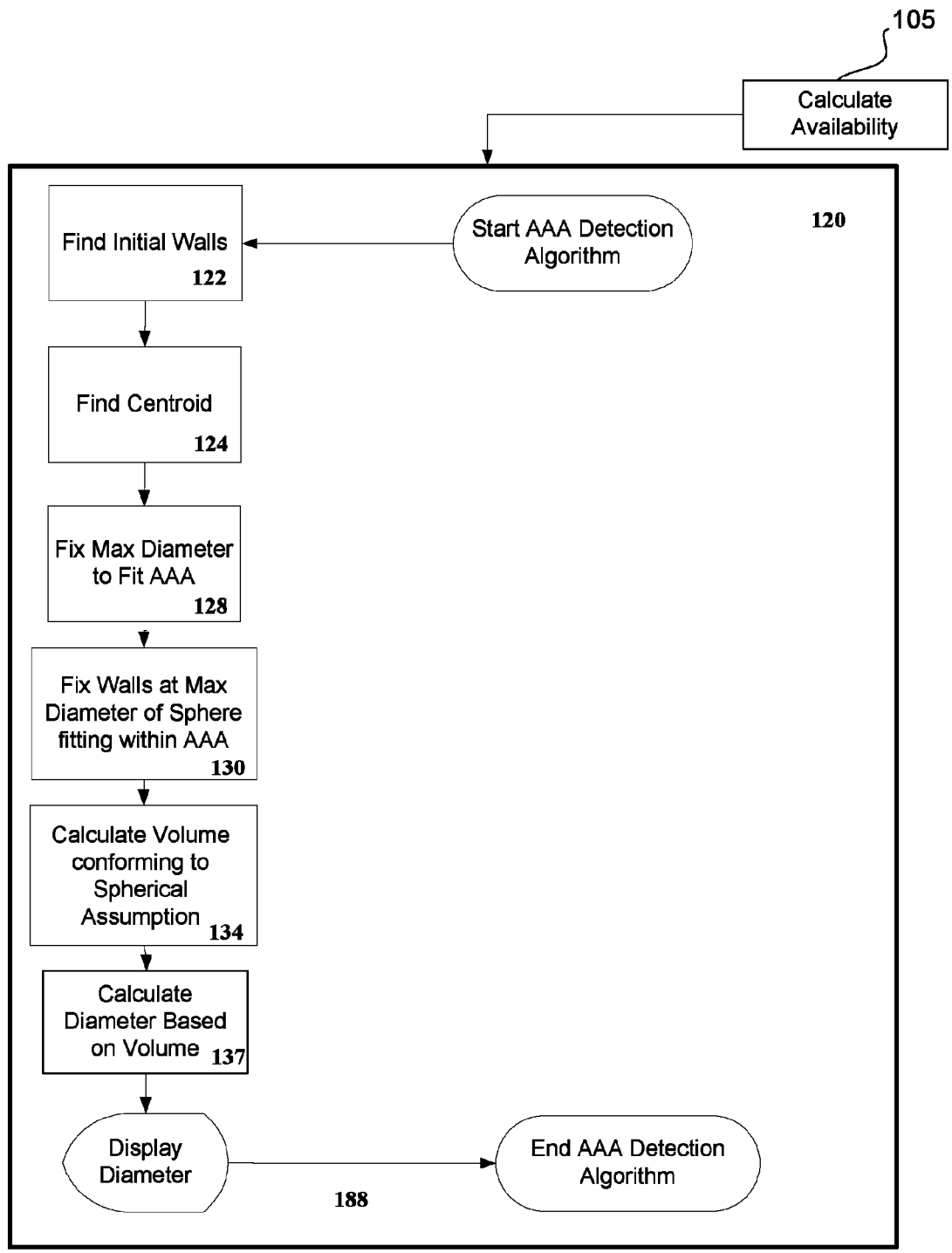
Figures 1, 12:
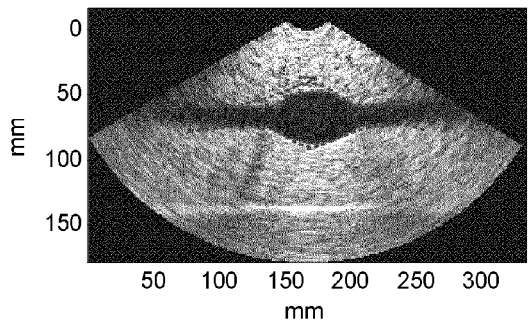
Figures 2, 12:
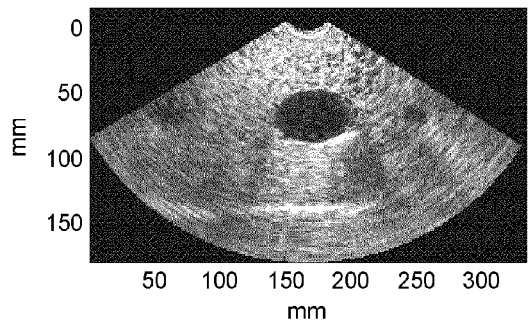
Figures 3, 12:
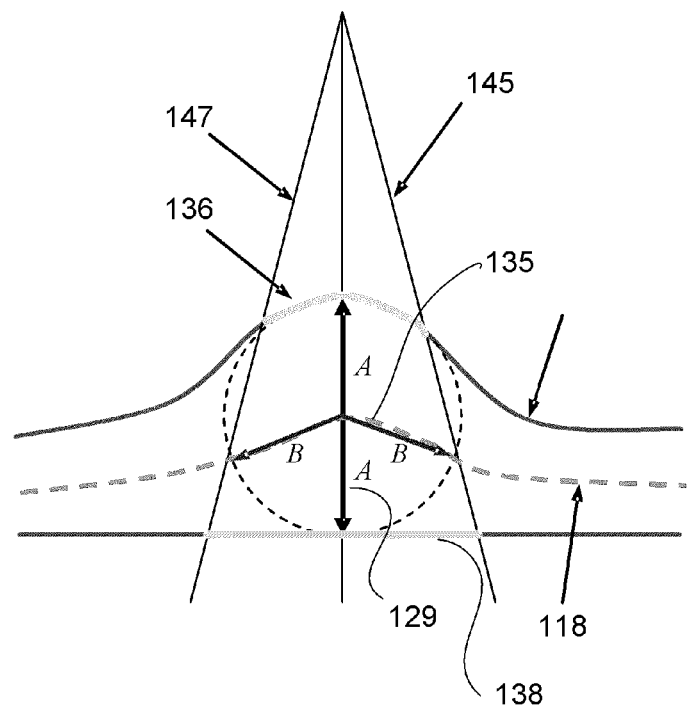

When the scan is done, the aiming result and B-mode image may be displayed, for example as shown in an exemplary screen shot FIG. 10.

In AAA ultrasound scanning, a subject is required to fast overnight to have less gas in their intestines so that the images are more shadow-free due to air block. Air blocks not only degrade the B-mode image quality, but also mislead the delineation of abdominal aorta which is an advantageous factor for volume estimation accuracy. Specifically, the acoustic energy can be blocked by a layer which has high acoustic impedance difference as between two media. Examples can include a fat layer under skin or air pockets in the intestines. The presence of fat and/or air pockets prevent information relevant to the region of interest (ROI), such as an AAA wall or lumen location, to be reflected to the transducer resulting in dark or black region underneath (See FIG. 6 as an example). As a result scanlines (A-mode) may be investigated to determine whether useful information is contained therein or not. As shown in FIG. 6-1, a B-mode image of an AAA may be in the same field as a shadow region due to the air-block or fat layer, two A-mode lines 60, 65. In A-mode line 60 there may be an AAA between depth 85 and 120 mm, therefore A-mode line 60 has useful information such as tissue, AAA, and acoustic enhancement. In A-mode line 65 however there may be no information due to the acoustic block near the depth of 25 mm. FIGS. 6-2 and 6-3 are representative histograms of the A-mode lines 60 (FIG. 6-2) and 65 (FIG. 6-3) wherein, a threshold line set at 40 (67), in the exemplary histogram, is shown. The threshold line 67 may be used to determine whether the A-mode has available information or not.

FIGS. 7-1-7-12 and 8 illustrate how the aorta aiming guide can determine "availability" and may be used to help the user correct the position of the transceiver to scan AAA.

In order to guide a user to the best scanhead position and orientation, the guidelines are used. A threshold may be established, which can vary from patient to patient, but in this example the threshold is 40 (as above), and may be related to the intensity number, for example, out of 256 levels after A-law compression. A searching range, in this non-limiting example is between 42% of A-mode length to 100% of A-mode length, the length of which may be related to experimental testing of optimal scan depths. Given these parameters, once set, if any A mode point within the searching range is above the established threshold but below an acoustic block, the A mode line may be determined as "Available". Based on the established threshold, "non-available" scanlines can be differentiated from "available" scanlines, for example, "non-available" are shadowed. In FIGS. 7-1-7-12 A-mode lines are marked non-available by colored markings/dots underneath the B-mode image indicating the non-availability of that area. In FIG. 7-10 for example, colored markings/dots underneath the B-mode image represent approximately 40% unavailable scanlines, compared to >90% unavailable scanlines in FIG. 7-6.

The available and non-available regions from all 12 planes of this example of the B-mode display may be then plotted in C-mode representing the pseudo-horizontal cross section of the 3D scan cone composed by the 12 sectors as shown in FIG. 8. FIG. 8 shows the C-mode display of an "Availability Plot" 80 for available and non-available regions. In this example, the "Availability Plot" 80 in C-mode (i.e. the view from the top of the scan cone) depicts available regions 85 as solid regions and non-available regions 87 as white and/or hashed lines. In this example, ~46% of the aggregate scanned regions are defined as "available." The percentage of available A-mode lines in the cone data, defined as "Availability" can be calculated using equation (1):

$$\% \text{ Availability} = \frac{\# of usefulscanlines}{\# of totalscanlines} \cdot 100 \quad (1)$$

The above calculation may be used to automatically determine whether the 3D full scan is appropriate for segmentation and display and without shadow within the region of interest.

In FIG. 9-1, the C-mode display 81 can be partitioned into concentric circles, in this example, an inner circle 93 and an outer circle 97, to directionally position the transceiver to an available area. Each quarter of the circle can be defined as a fan 98, from a perpendicular point defined by the cross-hairs in the middle; each overlapping fan expanding, for example, by 45° to both side in either direction. Each direction can have a fan, and the fans may be overlapped for the greatest coverage.

FIG. 9-2 illustrates an embodiment of a decision tree utilizing the above schema. For example, in order to guide a user to an optimal scanhead position and orientation, the availability may be calculated, starting within the inner circle 93. If the inner circle 93 has a greater than or equal to 75% available scanlines, the scan is a "good scan." Otherwise, a direction may be suggested to re-position the scanhead. Re-positioning may be suggested based on a criterion, generally in the direction corresponding to any inner fan and/or inner+outer fan availability determination that has the greatest calculated "availability." In other words, the arrow guide indicates the direction of greatest availability. First, for example, if any inner fan has availability greater than 75%, the suggested aiming direction may be the one whose inner fan availability is maximal. An arrow indicator guide may be a moderate and solid light indicator 121, 122, indicating that little movement is suggested. Second, if there is no inner fan that meets the above exemplary criteria, the suggested aiming direction may be based on the direction in which both the inner and outer fan has a maximum availability. In this case, the arrow indicator guide may be a flashing aggressive light indicator 124, 126, and the user may be guided in the recommended direction and orientation to achieve an optimized availability.

FIG. 10 is an exemplary screen view 100 of the aiming guide of the BVI9600. In this example, a B-mode image 102 and a C-mode image 103 is shown. Due to the air block in the 3D data, shown in the C-mode display 103 as non-available (by hatched lines) 87, the user is directed to move in a NW direction, i.e. towards the upper left had quadrant 110 where the greatest availability and/or "available" scanlines may be detected to collect a better data set.

Turning again to FIG. 9-1 and 9-2, the program 105 of an embodiment can determine whether to show a flashing arrow or solid arrow on the indicator panel dependent on the calculation of the percentage of availability of the image. For example:

Condition 1: Current Position=>75% available at BLOCK 110=good scan at BLOCK 112=no movement is indicated=start AAA detection algorithm (See FIG. 11).

Condition 2: Any inner fan=>75% at BLOCK 118=reposition transceiver to aim towards greatest availability=Solid arrow direction indication at BLOCK 121 (See solid arrow 122 indicated in direction)=back to Condition 1 at BLOCK 110.

Condition 3: All Inner fans=≦25% available within inner fans=query inner+outer fans=flashing arrow direction indication at BLOCK 124 (See flashing arrow 126 indicated in direction of maximal inner+outer fan availability)=back to Condition 1 at BLOCK 110.

Using the above positioning method, the user moves the instrument around on the abdomen to measure the abdominal aorta, which may be calculated from full three-dimensional scan cone or, can be a single two dimensional plane.

The use of the three-dimensional scan cone removes orientation requirements, permitting the user to position the device in any orientation. The user takes several three-dimensional image scans, moving along the patient's abdomen. After each scan, the volume/diameter of the section of the aorta covered by that scan may be displayed and the image may be stored if the diameter from the new scan is larger than any previous diameter. The image produced in this embodiment, whether it be form two dimensional planes or three dimension scan cone, can be optimally transmitted via the internet for remote enhance processing and rendering as is illustrated in FIG. 4.

Volume Measurement Algorithms:

A. Front and Back Walls. Once an optimal position for AAA measurement is achieved based on the "availability" calculation 105 of compared scanlines, as described above and illustrated in FIG. 9-2, an AAA detection algorithm 120 may be used to The fundamental AAA detection algorithm 120 used in the BVI 9600 device begins with process block Find Initial Wall 122 using A-mode ultrasound data that incorporates data-smoothing. Find Initial Wall 122 looks for the front and back walls of the abdominal aorta illustrated and described in FIG. 12 below. After the front and back walls are found, a line passing through the center of the abdominal aorta may be determined in the following process block Find Centroid 124. This center abdominal aorta line or centroid may be used as a seed from which process block Fix Initial Walls 130 utilized, as illustrated and described in FIG. 14 below. Fix Initial Walls 130 refines the initial wall points, removes any outliers, and fills gaps in the detected wall location regions. The Centroid 118 as shown in FIG. 12-3, may be found by averaging the front and back walls. The maximum diameter (2A) 129 of a sphere that can fit within the AAA may be calculated as the maximum distance between the front and back walls. The Fix Walls algorithm 130 may be adjusted to comply with this spherical assumption to limit the segmentation of the AAA. That is, the given segmentation (from automatic detection) may be modified not to exceed the circle boundary whose diameter is the maximum of one, maximized slice. In FIG. 12-1 and 12-2 B-mode images of a longitudinal section 12-1 and cross section 12-2 are shown with their exemplary segmentations for volume estimation. In this example, the AAA phantom has 4 cm, and 5 cm diameter in axial and lateral directions, respectively.

FIG. 12-3 is a schematic representation of the application of the limited segmentation wherein a maximum diameter may be fixed from the centroid 118. Two lengths, length (2A) 129 the diameter, and length B 135, the radius, represent the maximum circle that can fit inside the AAA. The mathematical steps to calculate a modified segmentation parameter are described with reference to FIG. 11, above. The volume calculation at BLOCK 134 may be the result of the aggregate calculation of volume resulting from the limited segmentation, in this example, represented by lines 136 and 138, i.e. those within the scanlines 145, 147 at points corresponding to the intersection of the front wall and the back wall of the artery being measured. At BLOCK 137 the diameter calculation may be derived by application mathematical relationship between volume and diameter as further discussed in relationship to FIG. 13 below.

Figure 13:
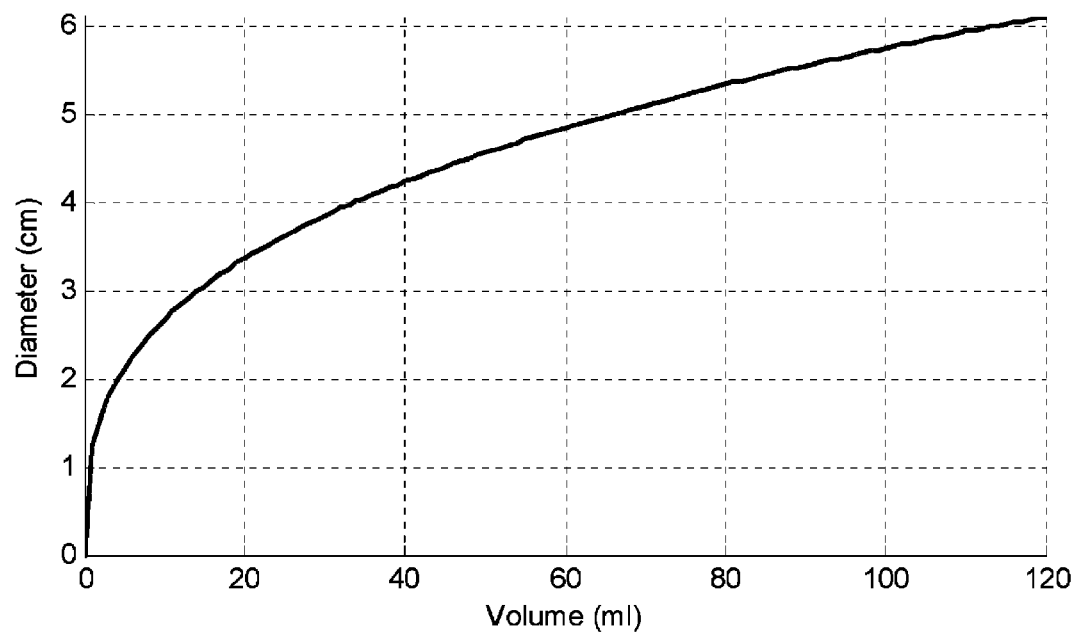
FIG. 13 is a graphic diagram for the conversion from volume to diameter assuming an object shape is sphere.

FIG. 13 graphically represents the relationship between volume and diameter as determined using the below formulae. The volume of sphere volume is:

$$V = \frac{4}{3}\pi \cdot \left(\frac{D}{2}\right)^3 \tag{2}$$

where, V is a volume and D is a diameter, and where the diameter can be derived if the volume is know by manipulation of the above relationship:

$$D = \sqrt[3]{\frac{6}{\pi}V} \tag{3}$$

The mathematical functions can be calculated automatically from a look-up table of diameter values such that the diameter calculations need not be performed for each volume under consideration. For example, the above relationship can be expressed as a look-up table, where once the volume (at BLOCK 134) is determined by the limited segmentation procedure, the diameter may be automatically correlated (at a BLOCK 137) with a pre-calculated diameter according to the above relationship.

Figure 14:
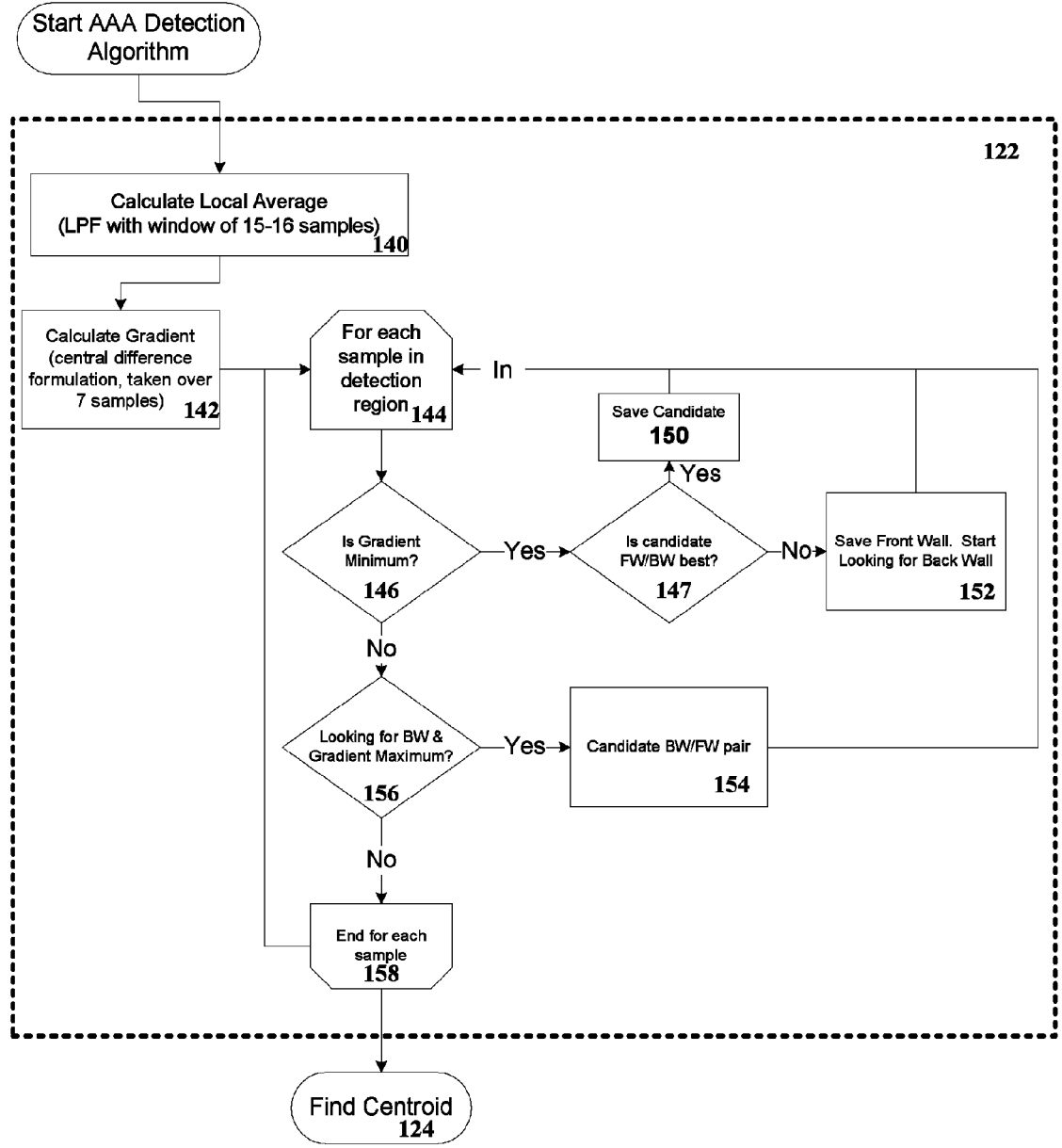
FIG. 14 depicts a flowchart of the Find Initial Walls sub-algorithm of FIG. 11.

B. AAA Detection Algorithm, Finding Front and Back Abdominal Aorta Walls and Centroid:

FIG. 14 depicts a flowchart of the Find Initial Walls sub-algorithm of FIG. 11. Find Initial Walls 122 process may be executed on every A-mode scan line and may be subjected to averaging and low-pass filtering using, for example, a 15 or 16 sample set beginning with process block 140. Next, a local gradient at process block 142 may be computed for each sample point using a central difference formulation taken for seven samples. The central difference formulation is defined by equations 4-9 (Eq. 4-9) below:

The standard central difference formula is given in Equation 4:

$$dx_i = x_{i+1/2} - x_{i-1/2} \tag{4}$$

This formula assumes that the function is defined at the half-index, which is usually not the case. The solution is to widen the step between the samples to 2 and arrive at the equation in 5.

$$dx_i = \frac{1}{2}(\overline{x}_{i+1} - \overline{x}_{i-1}) \tag{5}$$

The normalization factor is simply the distance between the two points. In Eq. 4 the distance separating the two means in the calculation was 1, and in Eq. 5 the step between the two means is 2. The normalization of the gradient by the step size, while mathematically correct, incurs a cost in terms of operation. This operation may be neglected in the gradient calculation for the aortic wall detection algorithm with minimal effect: since the same calculation is performed for every data sample, every data sample can have the same error and thus the relative gradient values between different samples remain unchanged.

To further amplify wall locations, the gradient calculation may be expanded to three neighboring points to each side of the sample in question. This calculation is shown in Eq. 6. This calculation is simply the sum of three gradient approximations and thus the end result can be 12 times its normal value. This deviation from the true mathematical value has minimal effect since the calculation may be the same at each point and thus all the gradient values can be 12 times their usual value. An advantage to using the three neighboring points is that more information about the edge is included in the calculation, which can amplify the strong edges of the aorta and weaken the false-edges caused by the noise process in the image.

$$dx_i = \overline{x}_{i+3} + \overline{x}_{i+2} + \overline{x}_{i+1} - \overline{x}_{i-1} - \overline{x}_{i-2} - \overline{x}_{i-3} \tag{6}$$

The full calculation is written in Eq. 7. The first line shows the summation calculation to obtain the means, and the difference operations to obtain the gradient. The entire sum is normalized by 15, the number of points included in each local mean. The second line of the operation shows the result when the summations are simplified, and represents the maximal implementation of the calculation. This calculation incurs a cost of 23 additions or subtractions, 2 floating-point multiplications, 1 floating point division, and at least 1 temporary variable. This operation cost is incurred for 91% of the data samples.

$$dx_i = \frac{\sum_{j=i+3-7}^{j=i+3+7} x_j - \sum_{j=i-3-7}^{j=i-3+7} x_j + \sum_{j=i+2-7}^{j=i+2+7} x_j - \sum_{j=i-2-7}^{j=i-2+7} x_j + \sum_{j=i+1-7}^{j=i+1+7} x_j - \sum_{j=i-1-7}^{j=i-1+7} x_j}{15}$$

$$= \frac{x_{i+10} - x_{i-10} + x_{i+5} - x_{i-5} + 2(x_{i+9} - x_{i-9} + x_{i+6} - x_{i-6}) + 3(x_{i+8} - x_{i-8} + x_{i+7} - x_{i-7})}{15} \tag{7}$$

The cost of the calculation can be reduced by not simplifying the summations and using a running sum operation. In that manner, only one mean may need to be calculated for each point, but that mean needs to be for the i+3 point. The running sum calculation uses the previous sum, and then corrects the sum by subtracting the old "left hand" end point and adding the new "right hand" end point. The operation is shown in Eq. 8. This running sum operation incurs a cost of 5 additions and subtractions.

$$\overline{x}_{i+3} = \sum_{j=i+3-7}^{j=i+3+7} x_j \tag{8}$$

$$= \overline{x}_{i+3-1} - x_{i+3-8} + x_{i+3+7}$$

$$= \overline{x}_{i+2} - x_{i-5} + x_{i+10}$$

Since the running sum was calculated for the i+3 point, all average values are available for the gradient calculation. This calculation is shown in Equation 9:

$$dx_i = \frac{-\overline{x}_{i-3} - \overline{x}_{i-2} - \overline{x}_{i-1} + \overline{x}_{i+1} + \overline{x}_{i+2} + \overline{x}_{i+3}}{16} \qquad (9)$$

This equation has the same form as the one in Eq. 6 except for the normalization factor of 16. This normalization factor is not a result of the gradient operation, but rather it is the normalization factor mean calculation. The factor of 16 is used instead of the standard value of 15 that one would expect in a 15-point average for this simple reason: using a factor of 16 eliminates floating-point division. If the means are normalized by 16, then the division operation can be replaced by a "right"-shift by 4 at a significantly lower cost to the embedded system. Therefore the gradient operation has eleven additions and subtractions and one shift by 4.

Adding the operational cost of the running sum calculation gives an overall cost of 16 additions and subtractions and the shift. A clear advantage in this simplification is the elimination of multiplication and division from the operation.

Returning to FIG. 14, the results from local gradient 142 are subjected to loop limit processing between blocks 144 and 158 to obtain the best front wall and back wall pair for each scan line denoted as a tissue gradient or tissue delta. The best front wall and back wall pair on each line may be defined as the front wall and back wall pair for which the pixel intensity difference in the back wall gradient and front wall gradient is the maximum and the smallest local average between front wall and back wall pair is the minimum.

The loop limit processing begins with loop limit block 144 that receives pixel values for each sample in the detection region and subjects the pixel intensity values to determine whether the gradient is minimum at decision diamond 146. If affirmative, then the pixel values may be ascertained whether it's the best front wall-back wall (FW/BW) candidate combination at decision diamond 147. If affirmative, the FW/BW candidate pair may be saved and loop limit processing returns to limit block 144. If negative, at process block 152, the Front Wall pixel value may be saved and another back wall candidate may be sought with a subsequent return to loop limit block 152.

Returning to decision diamond 146, if the answer is negative for "Is gradient Minimum?", sub-algorithm 122 continues to decision diamond 156 to determine whether the back wall and the gradient is maximum. If affirmative, at process block 154, a candidate BW/FW pair is established and sub-algorithm re-routes to loop limit block 144. If negative, the end of analysis for a particular FW/BW candidate occurs at loop limit block 158 either routes back to the limit loop block 144 or exits to find Centroid 124.

Formulations relating to Find Centroid 124 may be based on coordinate geometries described in equations 10 and 11 utilizing coordinate conversions. The coordinate conversions are shown in Eq. 10 where 38 is the index of the broadside beam (the ultrasound ray when $\phi=0$), $\phi$ is the index of the line, $\theta$ is the angle of the plane. The plane angle is shifted by $\pi$ to ensure that the sign of the x and y coordinates match the true location in space.

$$x = (38-\phi)\cos(\pi-\theta)$$

$$y = (38-\phi)\sin(\pi-\theta) \qquad (10)$$

The trigonometric functions can be calculated for a table of $\theta$ values such that the cosine and sine calculations need not be performed for each of the points under consideration. The closest plane can be found by finding the shortest vector from each plane to the centroid. The shortest vector from a plane to a point can be the perpendicular to the projection of the centroid on the plane. The projection of the centroid on the plane is defined as the dot product of the centroid vector, c, with the plane definition vector, a, divided by the length of the plane definition vector. If the plane definition vector is a unit vector, then the division operation is unnecessary. To find the perpendicular to the projection, it is sufficient to subtract the projection vector from the centroid vector as shown in Eq. 11:

$$\|c - proj_c a\|^2 = \left\| c - \frac{c \cdot a}{\|a\|^2} \right\|^2 \qquad (11)$$

The length of these projections can be found by calculating the Euclidean norm for each line. The Euclidean norm may be more commonly known as the length or magnitude of the vector. To find the plane closest to the centroid, calculate the lengths for the perpendicular to the projection of the centroid on each plane, and take the plane with the shortest of these lengths.

While the preferred embodiment of the invention has been illustrated and described, as noted above, many changes can be made without departing from the spirit and scope of the invention. For example, it should be understood that various changes, modifications, and substitutions can be incorporated in the apparatus embodiment to achieve the ultrasonic, volumetric determination of the abdominal aorta to thus apply that to the aortic diameter reading. Accordingly, the scope of the invention is not limited by the disclosure of the preferred embodiment.

The embodiments of the invention in which an exclusive property or privilege is claimed are defined as follows:

1. A system to detect an abdominal aortic aneurysm in a region of interest comprising:
   an ultrasound transceiver configured to deliver ultrasound energy and receive echoes of the ultrasound energy across a plurality of scan planes from the region of interest within which an abdominal aortic aneurysm potentially exists;
   a processing device configured to signal process the received echoes, characterize the signal-processed echoes across the plurality of scan planes, and detect from the signal-processed echoes an abdominal aortic aneurysm, wherein a percentage of availability of scan planes is calculated based on echoes received from scan planes, the processing device further configured to calculate positioning information of the ultrasound transceiver from the percentage availability; and
   at least one display configured to present a visual depiction of the percentage of availability of the region of interest contained in a plurality of scan planes,
   the at least one display configured to present the positioning information of the ultrasound transceiver.

2. The system of claim 1, wherein the processing device guides a user to position the ultrasound transceiver towards regions of interest where the calculated percentage of availability in a plurality of scanlines is 75-100% availability.

3. The system of claim 1, wherein the processing device includes at least one of a C-mode component, a B-mode component, and an A-mode component.

4. A system for abdominal aortic aneurysm evaluation and monitoring in a region of interest of an abdominal aorta, comprising:
   at least one ultrasound transceiver configured to deliver ultrasound energy and receive echoes of the ultrasound energy across a plurality of scan planes from the region of interest within which an abdominal aortic aneurysm potentially exists for obtaining three-dimensional ultrasound scan information;

a processor configured to signal process the received echoes and characterize the signal-processed echoes across the plurality of scan planes, wherein a percentage of availability of scan planes is calculated based on echoes received from scan planes, the processing device further configured to calculate positioning information of the ultrasound transceiver from the percentage availability, determine aorta volume information from the scan plane information and detect from the signal-processed echoes an abdominal aortic aneurysm, at least one display configured to indicate positioning information received from the ultrasound transceiver, wherein the display is a visual depiction of the calculated percentage availability;

a guide configured to guide a user to position the ultrasound transceiver over a region of interest of the aorta based on the calculated percentage availability; and a calculation circuit configured to calculate the diameter of the aorta at the region of interest from the aorta volume information.

5. The system of claim 4, wherein the guide guides the user to position the ultrasound transceiver towards regions of interest where the calculated percentage of availability contained in a plurality of scans planes is 75-100% availability.

6. A method to detect and measure an abdominal aortic aneurysm comprising:

transmitting ultrasound energy to a section of an abdominal aorta;

collecting ultrasound echoes returning from the section;

generating signals from the ultrasound echoes;

identifying fundamental signals from the generated signals;

processing the fundamental signals using algorithms designed for fundamental signals;

calculating the volume of the section;

calculating the diameter of the section from the calculated volume of the section;

detecting from the ultrasound echoes an abdominal aortic aneurysm;

calculating a percentage of availability associated with the fundamental signals;

presenting a visual depiction of the percentage of availability; and indicating to the user a position for an ultrasound transmitting device wherein the percentage of availability is maximized.

7. The method of claim 6, wherein a guide means guides the user to position the ultrasound transceiver to at least one position to measure the volume of the section.

8. A non-transitory computer-readable medium having instructions to execute a method to detect and measure an abdominal aortic aneurysm, comprising the steps of:

transmitting ultrasound energy to a section of an abdominal aorta;

collecting ultrasound echoes returning from the section;

generating signals from the ultrasound echoes;

identifying fundamental signals from the generated signals;

processing the fundamental using algorithms designed for fundamental signals;

calculating measurements of the volume of the section; and calculating measurements of the diameter of the section from the calculated volume of the section;

detecting from the ultrasound echoes an abdominal aortic aneurysm;

calculating a percentage of availability associated with the fundamental signals;

presenting a visual depiction of the percentage of availability; and indicating to the user a position for an ultrasound transmitting device wherein the percentage of availability is maximized.

* * * * *